(12) United States Patent
Hulings et al.

(10) Patent No.: US 12,350,507 B2
(45) Date of Patent: Jul. 8, 2025

(54) CONDUCTIVE GEL RELEASE AND DISTRIBUTION DEVICES

(71) Applicant: ZOLL Medical Corporation, Chelmsford, MA (US)

(72) Inventors: Robert J. Hulings, Mars, PA (US); Scott D. Quinnell, Kittanning, PA (US); Dale Ballard, Glenshaw, PA (US); Ronald A Seman, Pittsburgh, PA (US)

(73) Assignee: ZOLL Medical Corporation, Chelmsford, MA (US)

(*) Notice: Subject to any disclaimer, the term of this patent is extended or adjusted under 35 U.S.C. 154(b) by 569 days.

(21) Appl. No.: 17/502,234

(22) Filed: Oct. 15, 2021

(65) Prior Publication Data

US 2022/0032078 A1    Feb. 3, 2022

Related U.S. Application Data

(63) Continuation of application No. 16/381,029, filed on Apr. 11, 2019, now Pat. No. 11,173,317, which is a continuation of application No. 15/196,638, filed on Jun. 29, 2016, now Pat. No. 10,307,605.

(51) Int. Cl.
| | | |
|---|---|---|
| *A61N 1/39* | (2006.01) | |
| *A61M 35/00* | (2006.01) | |
| *A61N 1/04* | (2006.01) | |
| *A61B 5/00* | (2006.01) | |
| *A61B 5/282* | (2021.01) | |

(52) U.S. Cl.
CPC .......... *A61N 1/3968* (2013.01); *A61M 35/00* (2013.01); *A61N 1/046* (2013.01); *A61N 1/0484* (2013.01); *A61N 1/3904* (2017.08); *A61B 5/282* (2021.01); *A61B 5/6804* (2013.01); *A61B 5/6831* (2013.01)

(58) Field of Classification Search
CPC .... A61N 1/3968; A61N 1/046; A61N 1/0484; A61N 1/3904; A61M 35/00; A61B 5/282; A61B 5/6804; A61B 5/6831
See application file for complete search history.

(56) References Cited

U.S. PATENT DOCUMENTS

| | | |
|---|---|---|
| 4,729,377 A | 3/1988 | Granek |
| 5,078,134 A | 1/1992 | Heilman |
| 8,406,842 B2 | 3/2013 | Kaib |
| 8,880,196 B2 | 11/2014 | Kaib |
| 9,008,801 B2 | 4/2015 | Kaib et al. |

(Continued)

*Primary Examiner* — Eugene T Wu
(74) *Attorney, Agent, or Firm* — Finch & Maloney PLLC

(57) ABSTRACT

A gel deployment device for use with an electrotherapy system is provided. The device includes a plurality of gel reservoirs disposed on a substrate, each of the plurality of gel reservoirs containing conductive gel. Each of the gel reservoirs are positioned adjacent to at least one seal such that the seal restricts flow of the conductive gel. The seal can be configured to release the conductive gel from the gel reservoir in response to pressure being applied about a perimeter of the seal at, for example, multiple points about the perimeter or substantially equally about the perimeter of the seal. In an example, each gel reservoir can be shaped such that the gel reservoir partially or fully surrounds a seal. In another example, multiple gel reservoirs can be arranged in clusters such that the multiple gel reservoirs are positioned about a single seal.

19 Claims, 13 Drawing Sheets

(56) References Cited

U.S. PATENT DOCUMENTS

| | | | |
|---|---|---|---|
| 9,861,806 B2 | 1/2018 | Kaib | |
| 2012/0150164 A1 | 6/2012 | Lee et al. | |
| 2013/0085538 A1* | 4/2013 | Volpe | A41D 13/1281 607/6 |
| 2014/0207201 A1* | 7/2014 | Piha | A61N 1/3918 607/142 |
| 2014/0249613 A1* | 9/2014 | Kaib | A61N 1/0496 607/152 |
| 2015/0283391 A1* | 10/2015 | Meeker | A61N 1/3968 607/7 |
| 2015/0327789 A1 | 11/2015 | Sjaaheim | |

* cited by examiner

CONDUCTIVE GEL RELEASE AND DISTRIBUTION DEVICES

CROSS-REFERENCE TO RELATED APPLICATIONS

This application claims the benefit under 35 U.S.C. § 120 as a Continuation of U.S. patent application Ser. No. 16/381,029, titled "CONDUCTIVE GEL RELEASE AND DISTRIBUTION DEVICES," filed Apr. 11, 2019, which is a continuation of U.S. patent application Ser. No. 15/196,638, titled "CONDUCTIVE GEL RELEASE AND DISTRIBUTION DEVICES," filed Jun. 29, 2016, now U.S. Pat. No. 10,307,605, each of which is hereby incorporated by reference in its entirety.

BACKGROUND

The present disclosure is directed to medical therapy systems, and more particularly, to electrode systems such as therapy electrodes including gel release and distribution mechanisms.

Cardiac arrest and other cardiac health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival. These efforts are expensive and have a limited success rate, and cardiac arrest, among other conditions, continues to claim the lives of victims.

To protect against cardiac arrest and other cardiac health ailments, some at-risk subjects may use a non-invasive bodily-attached ambulatory medical monitoring and treatment device, such as the LifeVest® wearable cardioverter defibrillator available from ZOLL Medical Corporation. To remain protected, the subject wears the device nearly continuously while going about their normal daily activities, while awake, and while asleep.

Such medical devices work by providing one or more shocks to a patient. Prior to delivering the one or more shocks, a conductive gel deployment device can release a conductive gel about a conductive surface of a therapy electrode such that the one or more shocks can be directed from the therapy electrode to the patient's skin.

SUMMARY

In some embodiments, a gel deployment device for use with an electrotherapy system is provided. The device includes a substrate, a plurality of gel reservoirs disposed on the substrate, and at least one conductive surface. Each of the plurality of gel reservoirs comprises a volume of a conductive gel and are positioned on the substrate substantially adjacent to a seal. The seal is configured to release the conductive gel from at least one of the plurality of gel reservoirs in response to pressure being applied about a perimeter of the seal. The conductive surface is configured to come into contact with the released conductive gel and to deliver a therapeutic current to a body of a patient.

Preferred and non-limiting embodiments or aspects of the present invention will now be described in the following numbered clauses:

Clause 1. A gel deployment device for use with an electrotherapy system, the device comprising: a substrate; a plurality of gel reservoirs disposed on the substrate, each of the plurality of gel reservoirs comprising a volume of a conductive gel and positioned substantially adjacent to a seal; wherein the seal is configured to release the conductive gel from at least one of the plurality of gel reservoirs in response to pressure being applied about a perimeter of the seal; and at least one conductive surface configured to come into contact with the released conductive gel and to deliver a therapeutic current to a body of a patient.

Clause 2. The device of clause 1, wherein the conductive gel is capable of conducting the therapeutic current from the at least one conductive surface to the patient's skin.

Clause 3. The device of clause 1 or 2, wherein the at least one conductive surface comprises at least one opening configured to distribute the therapeutic current through the at least one conductive surface.

Clause 4. The device of any of clauses 1-3, wherein the substrate comprises one or more ventilation holes configured to facilitate air flow through the gel deployment device.

Clause 5. The device of any of clauses 1-4, wherein at least one of the plurality of gel reservoirs is oriented on the substrate such that the at least one of the plurality of gel reservoirs surrounds the seal.

Clause 6. The device of clause 5, wherein the at least one of the plurality of gel reservoirs is configured to exert an applied pressure at multiple points about the perimeter of the surrounded seal.

Clause 7. The device of clause 5 or 6, wherein the at least one of the plurality of gel reservoirs is configured to exert an applied pressure substantially equally about the perimeter of the surrounded seal.

Clause 8. The device of any of clauses 5-7, wherein each of the plurality of gel reservoirs comprises a donut shape defining an open center portion, wherein the seal is positioned within the open center portion of each of the donut shaped gel reservoirs.

Clause 9. The device of any of clauses 5-8, wherein each of the plurality of gel reservoirs comprises a polygon shape defining an open center portion, wherein the seal is positioned within the open center portion of each of the polygon shaped gel reservoirs.

Clause 10. The device of any of clauses 1-9, wherein at least one of the plurality of gel reservoirs is shaped such that it partially surrounds the seal.

Clause 11. The device of any of clauses 1-10, further comprising at least one reservoir cluster comprising two or more gel reservoirs.

Clause 12. The device of clause 11, wherein the at least one reservoir cluster is configured such that the two or more gel reservoirs are positioned about a center point, thereby defining an open center portion, wherein the seal is positioned within the open center portion of the at least one reservoir cluster.

Clause 13. The device of clause 12, wherein, upon application of the distributed pressure, the seal positioned within the open center portion of the at least one reservoir cluster is configured to release the conductive gel from each of the two or more of the plurality of gel reservoirs in the at least one reservoir cluster substantially simultaneously.

Clause 14. The device of any of clauses 1-13, further comprising at least one fluid channel, wherein a first end of the at least one fluid channel is connected to each of the plurality of gel reservoirs.

Clause 15. The device of clause 14, wherein a second end of the at least one fluid channel is connected to a pressure source configured to provide pressure through the at least one fluid channel to each of the plurality of gel reservoirs.

Clause 16. The device of any of clauses 1-15, wherein the plurality of conductive gel reservoirs is configured to collectively store between 3 ml and 20 ml of conductive gel.

Clause 17. The device of any of clauses 1-16, wherein each of the plurality of conductive gel reservoirs is configured to store between 0.50 and 4.0 ml of conductive gel.

Clause 18. The device of any of clauses 1-17, wherein the pressure being applied about the perimeter of the seal is between 4 psi and 30 psi.

Clause 19. A system for providing therapy to a patient, the system comprising: a garment; a monitor configured to monitor at least one physiological parameter of a patient; and a plurality of therapy electrodes operably connected to the monitor and disposed in the garment, each of the plurality of therapy electrodes comprising a gel deployment device for deploying conductive gel onto skin of the patient, the gel deployment device comprising a plurality of gel reservoirs disposed on a substrate, wherein each of the plurality of gel reservoirs comprises a volume of the conductive gel and is positioned substantially adjacent to a seal, wherein the seal is configured to release the volume of gel from the gel reservoir in response to a distributed pressure being applied about a perimeter of the seal, and at least one conductive surface configured to come into contact with the released conductive gel and deliver a therapeutic shock.

Clause 20. The system of clause 19, wherein at least one of the plurality of gel reservoirs is oriented on the substrate such that it surrounds the seal.

Clause 21. The system of clause 19 or 20, further comprising at least one reservoir cluster comprising two or more gel reservoirs.

Clause 22. The system of clause 21, wherein the at least one reservoir cluster is configured such that the two or more gel reservoirs are positioned about a center point, thereby defining an open center portion such that the seal of the two or more gel reservoirs is positioned within the open center portion of the at least one reservoir cluster.

Clause 23. A system for providing therapy to a patient, the system comprising: a garment; a monitor configured to monitor at least one physiological parameter of a patient; and a plurality of therapy electrodes operably connected to the monitor and disposed in the garment, each of the plurality of therapy electrodes comprising a gel deployment device for deploying conductive gel onto skin of the patient, the gel deployment device comprising a plurality of gel reservoirs disposed on a substrate, wherein each of the plurality of gel reservoirs comprises between 0.5 ml and 4.0 ml of the conductive gel and is positioned substantially adjacent to a seal, wherein the seal is configured to release the conductive gel from the gel reservoir in response to a distributed pressure of about 4 psi to 30 psi being applied about a perimeter of the seal, and at least one conductive surface configured to come into contact with the released conductive gel and deliver a therapeutic shock.

Clause 24. The system of clause 23, wherein at least one of the plurality of gel reservoirs is oriented on the substrate such that it surrounds the seal.

Clause 25. The system of clause 23 or 24, further comprising at least one reservoir cluster comprising two or more gel reservoirs.

Clause 26. A gel deployment device for use with an electrotherapy system, the device comprising: a substrate; at least one gel reservoir disposed on the substrate, the at least one gel reservoir comprising a volume of conductive gel and is positioned substantially adjacent to a seal, wherein the seal is configured to release the volume of conductive gel from the at least one gel reservoir in response to a pressure being applied to at least a portion of the seal; at least one gel conduit configured to fluidly connect to the at least one gel reservoir and direct flow of the released conductive gel from the at least one gel reservoir to one or more exit ports disposed on the substrate; and at least one conductive surface configured to come into contact with the released conductive gel and deliver a therapeutic shock.

Clause 27. The device of clause 26, wherein the one or more exit ports are spaced apart on the substrate to provide for even distribution of the conductive gel on the conductive surface.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of any particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1:
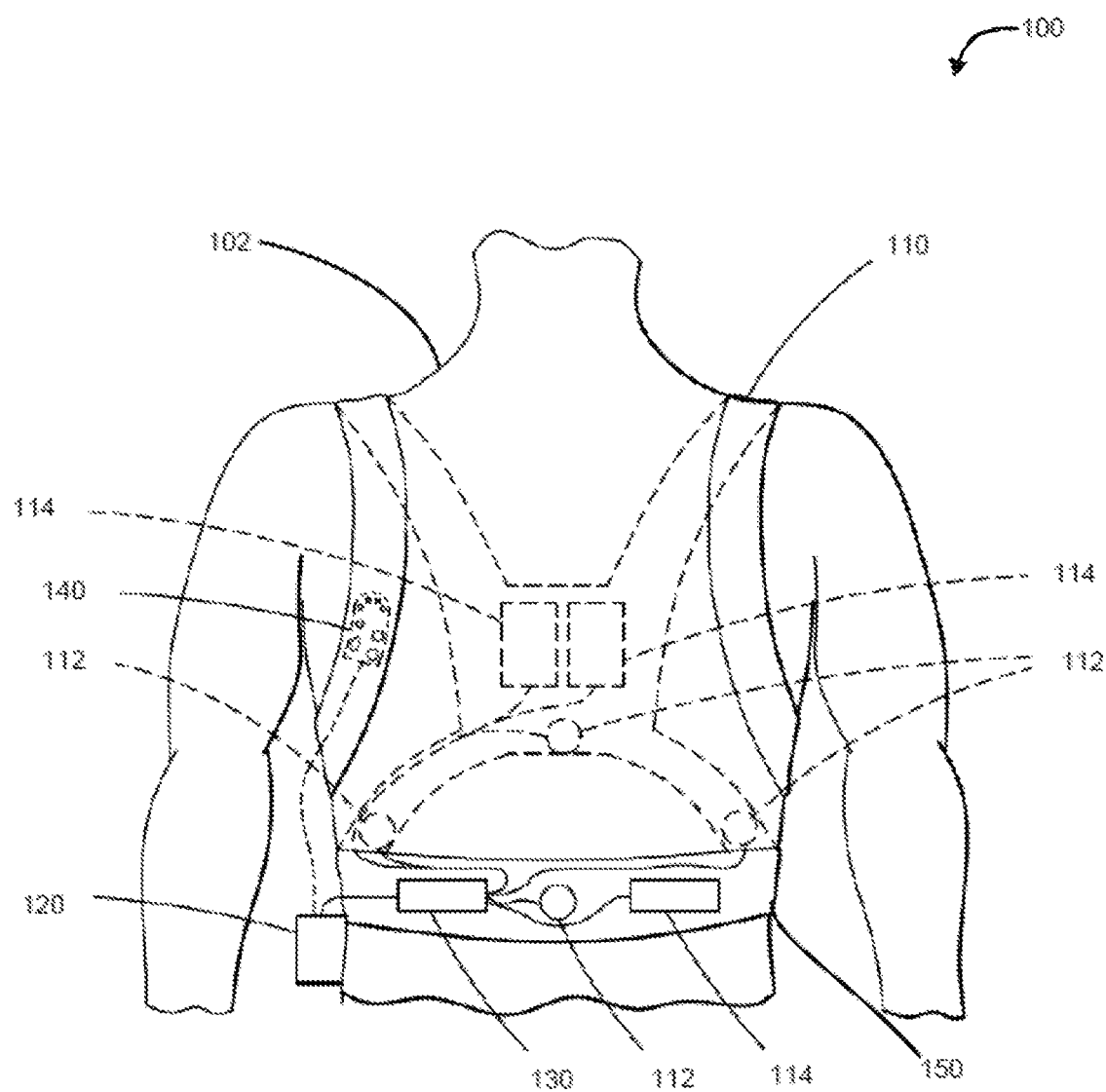
FIG. 1 depicts a wearable medical device, in accordance with an example of the present disclosure.

This disclosure relates to an improved conductive gel deployment device configured to provide for release and distribution of conductive gel for use with, for example, an electrode of an ambulatory electrotherapy system or device such as a wearable defibrillator as described in further detail below.

Wearable defibrillators operate by continuously or substantially continuously monitoring one or more physiological signals of an ambulatory patient and, upon determination that treatment is required, delivering one or more therapeutic electrical pulses to the patient. For example, a wearable defibrillator can monitor a cardiac signal of the patient via at least one sensing electrode, and provide the therapeutic electrical pulses to the patient via one or more electrotherapy electrodes. Prior to delivering the one or more therapeutic pulses, the wearable defibrillator can be configured to release conductive gel on the patient's skin, e.g., to lower an impedance between the electrode and the patient's skin. Such conductive gel can be stored in a conductive gel deployment device which can be configured to deploy the gel when needed.

In traditional designs, for example, a conductive gel deployment device can include a gel reservoir that is associated with an exit port configured to direct flow of conductive gel from the gel reservoir to a conductive surface of the therapy electrode. An adhesive seal positioned between the gel reservoir and its associated exit port is configured to prevent premature release of the conductive gel. In such designs, only a portion of the gel reservoir is configured to be in contact with the adhesive seal, thereby resulting in a smaller fluid pathway for flow of the conductive gel when released. As such, conductive gel flow from the gel reservoirs through the adhesive seals is reduced as a result of the limited contact and smaller fluid pathway. In a situation where a quick deployment of a large volume of conductive gel is desirable, the conductive gel flow can be unnecessarily slowed as a result of the limited contact between the gel reservoirs and the adhesive seals.

Additionally, as there is limited contact between the gel reservoirs and the adhesive seals, any pressure applied to the gel reservoirs (e.g., as a result of a patient wearing the garment 110 and, for example, leaning against or otherwise pressing on the conductive gel reservoirs) could result in a premature failure of the adhesive seal and unwanted release of the conductive gel. As described herein in greater detail below, the present disclosure describes configurations that partially or fully surround an adhesive seal with a gel reservoir, thereby distributing pressure applied by the gel reservoir about a larger portion of the adhesive seal (up to and including a full perimeter of, for example, a circular adhesive seal) and reducing the likelihood of a premature failure of the adhesive seal. In another implementation, a plurality of exit ports is associated with a gel reservoir to allow for increased volume in the flow of conductive fluid on to the patient's skin (see, e.g., FIG. 5A and associated description below). Also, gel conduits are provided to physically separate the gel reservoir and associated one or more adhesive seals from the exit port to prevent premature leakage of the conductive gel.

As described in detail below, various configurations can be used for a conductive gel deployment device that include various numbers and arrangements of conductive gel reservoirs and seals. In some examples, a series of conductive gel reservoirs are disposed on a substrate of the gel deployment device. Each conductive gel reservoir can be shaped such that it defines an open center portion. For example, each of the conductive gel reservoirs can have a substantially donut shape or a toroid shape (e.g., a geometric shape such as a circle or square rotated about a central point to define a three-dimensional shape), which defines an open center portion. The shapes and arrangements described herein can vary as needed to support one or more goals of the configurations below. For example, other shapes that define an open center portion can be used, including a rectangle, square, triangle, polygon, etc. Further, an external shape of the conductive gel reservoirs can differ from a shape of the open center portion (e.g., the external shape of the reservoir can be substantially square while the shape of the open center portion can be substantially circular). In an implementation, a seal, such as a peelable adhesive seal, can be positioned within the open center portion. For example, if the conductive gel reservoir has a donut shape, the adhesive seal can be configured to have a ring shape. The adhesive seal can be configured to release a conductive gel contained within the conductive gel reservoir in response to a distributed pressure being applied about a perimeter of the adhesive seal. After release, the conductive gel can be distributed about a conductive surface of the therapy electrode prior to delivery of a therapeutic current to a patient.

In certain implementations, multiple conductive gel reservoirs can be arranged into a reservoir cluster. An adhesive seal, such as the ring-shaped peelable adhesive seal described above, can be positioned at a center point in the middle of the reservoir cluster. In response to an applied distributed pressure, the adhesive seal can be configured to release a conductive gel from each of the conductive gel reservoirs in the reservoir cluster substantially simultaneously.

In some examples, one or more conductive gel reservoirs can be associated with one or more corresponding conductive gel conduits. In certain implementations, an adhesive seal can be configured to release a conductive gel from the one or more reservoirs. The one or more conductive gel conduits can be connected to the one or more gel reservoirs such that, upon release of the conductive gel, the one or more conductive gel conduits can direct flow of the conductive gel to multiple exit ports for distribution of the conductive gel.

It should be noted that the above described conductive gel deployment devices are merely shown as introductory examples, and additional details are provided in the following discussions of the figures.

Example Medical Devices

FIG. 1 illustrates an example medical device 100 that is external, ambulatory, and wearable by a patient 102, and configured to implement one or more configurations described herein. For example, the medical device 100 can be a non-invasive medical device configured to be located substantially external to the patient. Such a device can be, for example, an ambulatory medical device that is capable of and designed for moving with the patient as the patient goes about his or her daily routine. For example, the medical device 100 as described herein can be an external electrotherapy device that is bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 100 can include one or more of the following: a garment 110, one or more sensing electrodes 112 (e.g., ECG electrodes), one or more therapy electrodes 114, a medical device controller 120, a connection pod 130, a patient interface pod 140, a belt 150, or any combination of these. In some examples, at least some of the components of the wearable medical device 100 can be configured to be affixed to the garment 110 (or in some examples, permanently integrated into the garment 110), which can be worn about the patient's torso.

The controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The controller 120 can be operatively coupled to the therapy electrodes 114. For example, the therapy electrodes 114 can also be assembled into the garment 110, or, in some implementations, the therapy electrodes 114 can be permanently integrated into the garment 110. Additionally, the therapy electrodes 114 can include one or more conductive gel deployment devices such as the devices described herein and, as other examples, devices described in U.S. Patent Application Publication No. 2012/0150164 entitled "Therapeutic Device Including Acoustic Sensor," the content of which is incorporate herein by reference.

Component configurations other than those shown in FIG. 1 are possible. For example, the sensing electrodes 112 can be configured to be attached at various positions about the body of the patient 102. The sensing electrodes 112 can be operatively coupled to the medical device controller 120 through the connection pod 130. In some implementations, the sensing electrodes 112 can be adhesively attached to the patient 102. In some implementations, the sensing electrodes 112 and therapy electrodes 114 can be included on a single integrated patch and adhesively applied to the patient's body.

The sensing electrodes 112 can be configured to detect one or more cardiac signals. Examples of such signals include ECG signals, heart sounds, and/or other sensed cardiac physiological signals from the patient. The sensing electrodes 112 can also be configured to detect other types of patient physiological parameters, such as tissue fluid levels, lung sounds, respiration sounds, patient movement, etc. In some examples, the therapy electrodes 114 can also be configured to include sensors configured to detect ECG signals as well as other physiological signals of the patient. The connection pod 130 can, in some examples, include a signal processor configured to amplify, filter, and digitize these cardiac signals prior to transmitting the cardiac signals to the controller 120. One or more therapy electrodes 114 can be configured to deliver one or more therapeutic defibrillating shocks to the body of the patient 102 when the medical device 100 determines that such treatment is warranted based on the signals detected by the sensing electrodes 112 and processed by the controller 120.

As noted above, in some implementations, a gel deployment device can include conductive gel reservoirs that are configured to receive and store a volume of conductive gel. The conductive gel reservoirs can be shaped or arranged on a substrate such that the reservoirs are positioned substantially adjacent to at least one adhesive seal. As described herein, the conductive gel reservoirs can be configured to surround one or more adhesive seals such that the conductive gel reservoir is about 0.5 mm from the adhesive seal. In certain implementations, the conductive gel reservoirs can be positioned between 0.25 mm and 1.5 mm from the adhesive seal in a substantially adjacent position. As discussed in greater detail below, in some examples the conductive gel reservoirs can be shaped such that a single conductive gel reservoir surrounds a single adhesive seal. In such an example, when a pressurized fluid exerts a pressure on the conductive gel reservoir, the pressure exerted by the pressurized fluid can be subsequently distributed substantially equally about the perimeter of the adhesive seal. Once the pressure exerted on the conductive gel reservoir reaches a predetermined pressure level configured to rupture the adhesive seal (e.g., in the range of 4-30 psi), the adhesive seal ruptures, thereby resulting in release of the conductive gel stored in the conductive gel reservoir. In certain implementations, the adhesive seals can be configured as frangible adhesive seals that are designed and manufactured to rupture at a particular pressure level. For example, an exemplary adhesive seal can be configured to rupture at a predetermined pressure level between 4-15 psi, or between 10-20 psi, or between 20-30 psi, etc. The adhesive seal for a particular therapy electrode application can be configured and selected to rupture at a particular pressure level by optimizing the size, shape and adhesive strength of seal used to contain the conductive gel.

In some implementations, the adhesive seals can be configured to rupture at a predetermined applied force. For example, the pressurized fluid can exert a force that is distributed substantially equally about the perimeter of the adhesive seal. Once the force exerted on a conductive gel reservoir reaches a predetermined force configured to rupture the adhesive seal (e.g., 5.5 N/cm$^2$/sec to 15.2 N/cm$^2$/sec), the adhesive seal ruptures, thereby resulting in release of the conductive gel stored in the conductive gel reservoir. Though the following description related to pressures exerted on the adhesive seals, it should be appreciated that the rupturing of the adhesive seals can be described by way of exerted force as well.

In certain examples, the adhesive seal can rupture in a variety of ways. For example, a continuous portion of the adhesive seal (up to and including the full perimeter of the adhesive seal) can rupture substantially simultaneously, resulting in release of the conductive gel about the full length of the continuous portion that has ruptured. Similarly, multiple points about the perimeter of the adhesive seal can rupture, thereby resulting in a fluid path for release of the conductive gel at each of the multiple rupture points.

An example of a single conductive gel reservoir surrounding a single adhesive seal can be a substantially donut-shaped conductive gel reservoir. In such an example, the donut shape of the conductive gel reservoir defines an open center portion into which a ring-shaped adhesive seal can be placed. The geometry of such a design can result in any pressure applied to the ring-shaped adhesive seal (as a result of a pressure being exerted on a conductive gel reservoir) being equally distributed about the perimeter of the ring-shaped adhesive seal. Donut-shaped conductive gel reservoirs are described in greater detail below in the discussion of FIGS. 2A-2C.

In some implementations, multiple conductive gel reservoirs can be arranged in a reservoir cluster that surrounds a single adhesive seal. In such an implementation, rupturing of the single adhesive seal can result in release of the conductive gel contained within each conductive gel reservoir in the reservoir cluster. In such an example, multiple conductive gel reservoirs can be arranged around a single adhesive seal such that a pressurized fluid applied to each of the conductive gel reservoirs can result in a pressure being exerted on multiple points about the perimeter of the adhesive seal. As such, the exerted pressure can be distributed about the adhesive seal until the pressure reaches the predetermined pressure level configured to rupture the adhesive seal. This provides the advantage of having more area for conductive gel flow through the ruptured adhesive seal as shown in FIGS. 3A-3D, which are described in greater detail below. As before, the adhesive seal can rupture in a variety of ways. For example, a continuous portion of the adhesive seal (up to and including the full perimeter of the adhesive seal) can rupture substantially simultaneously, resulting in release of the conductive gel about the full length of the continuous portion that has ruptured. Similarly, one or multiple points about the perimeter of the adhesive seal can rupture, thereby resulting in a fluid path for release of the conductive gel at each of the multiple ruptured points. The adhesive seals, and how the adhesive seals rupture, are described in greater detail below in the discussion of FIGS. 3A-3D.

An example of multiple conductive gel reservoirs associated with a single adhesive seal can be a cluster of four conductive gel reservoirs arranged around a single ring-shaped adhesive seal. More or fewer such conductive gel reservoirs can be employed in a single reservoir cluster without substantially deviating from the scope of this disclosure. In some implementations, the arrangement of the conductive gel reservoirs into a reservoir cluster can define an open center portion into which a ring-shaped adhesive seal can be placed. The geometry of such a design can result in any pressure being applied to the individual conductive gel reservoirs also being distributed about the perimeter of the ring-shaped adhesive seal. For example, the exerted pressure can be applied at multiple points about the perimeter of the ring-shaped adhesive seal or substantially continuously about the perimeter of the adhesive seal. Reservoir clusters including multiple conductive gel reservoirs are described in greater detail below in the discussion of FIGS. 4A and 4B.

Figure 2A:
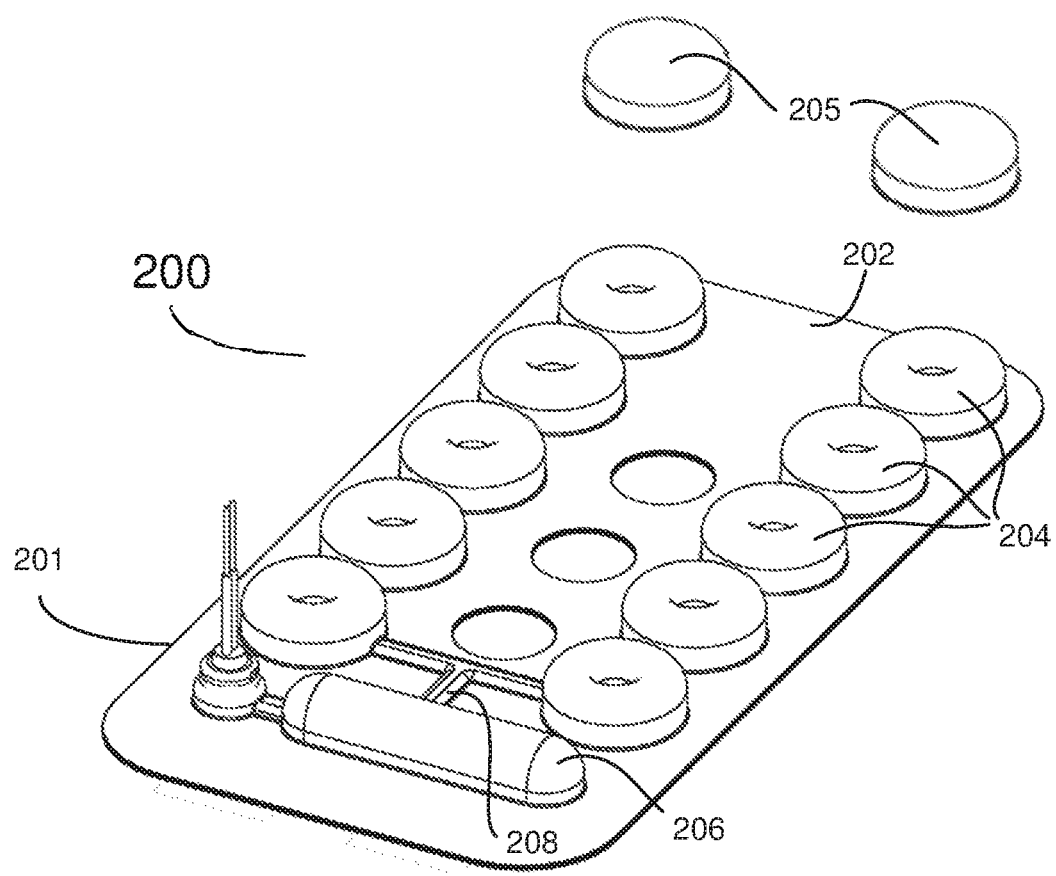
FIG. 2A depicts a plan view of a therapy electrode that can be used with the wearable medical device of FIG. 1.
Figure 2B:
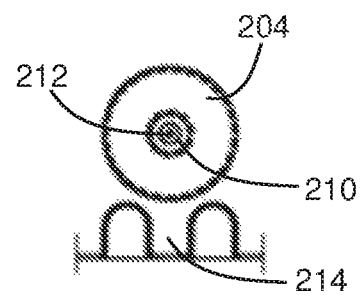
FIG. 2B depicts a conductive gel reservoir design for use with a therapy electrode such as the therapy electrode shown in FIG. 2A.
Figure 2C:
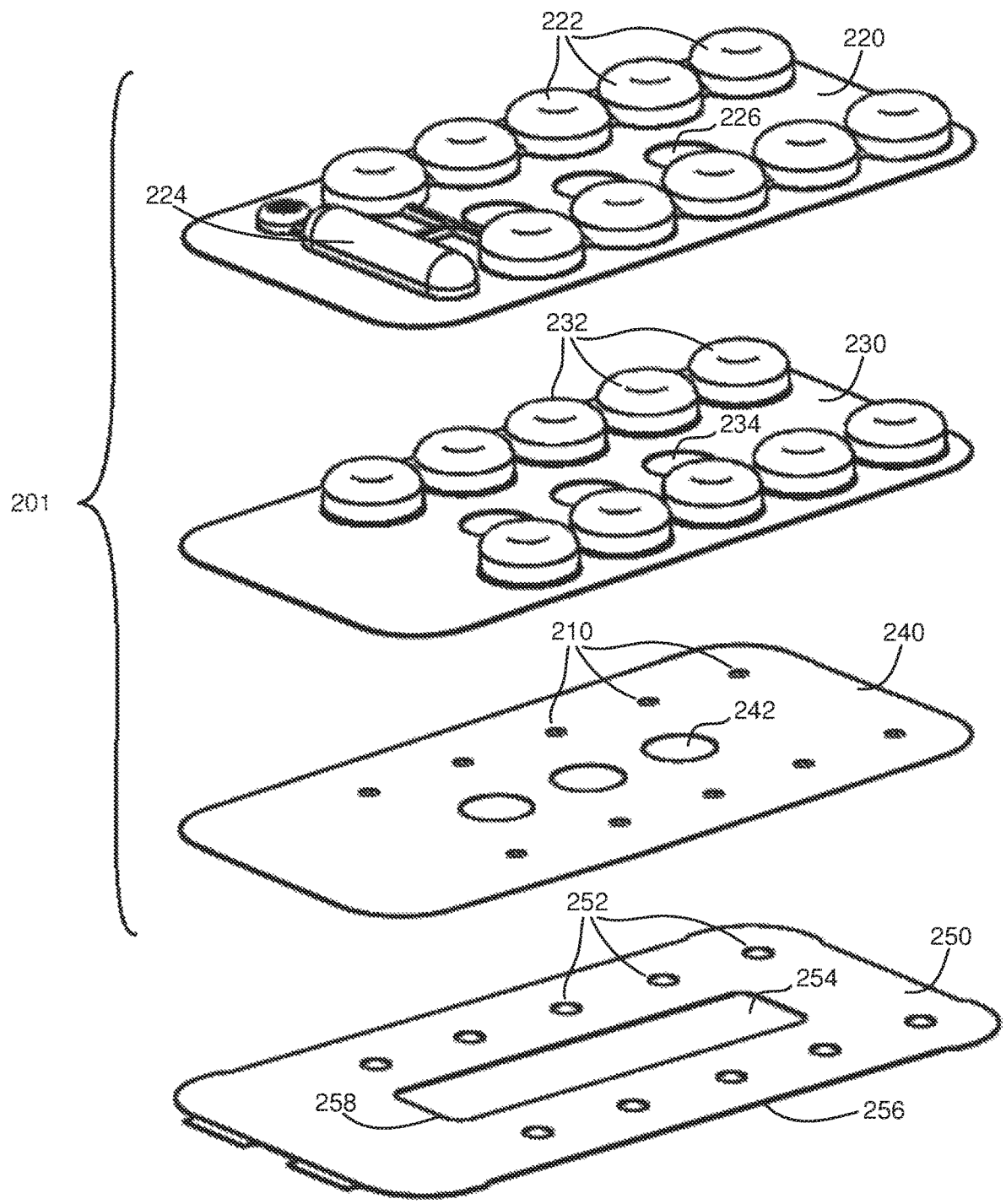
FIG. 2C depicts an exploded view of the therapy electrode of FIG. 2A.

FIGS. 2A-2C illustrate a gel deployment device that, in combination with a conductive layer, can be used to manufacture or otherwise assemble a therapy electrode. This design includes a conductive gel deployment device that uses a plurality of donut-shaped conductive gel reservoirs on the conductive gel deployment device. This configuration places a ring-shaped adhesive seal in the center of the donut-shaped conductive gel reservoir. Upon application of a pressurized fluid, pressure exerted by the pressurized fluid can be substantially equally distributed about the entire circumference of the adhesive seal. After the pressure reaches the predetermined pressure level configured to rupture the adhesive seal, the adhesive seal can rupture resulting in a release of the conductive gel contained within the conductive gel reservoir.

FIG. 2A is a plan view of a therapy electrode 200 that includes a conductive gel deployment device 201 using, for example in this configuration, donut-shaped conductive gel reservoirs 204. The therapy electrode 200 can be a multiple layer laminated structure that includes a gel deployment device 201 and an electrically conductive layer 250 (shown in FIG. 2C and explained in greater detail below). In use, the electrically conductive layer 250 can be disposed proximate to the patient's skin, although the conductive layer need not make direct contact with the patient (e.g., in implementations where conductive portions of the garment 110 act as an interface between the conductive layer 250 and the patient's skin, and/or implementations where portions of the patient's clothing may be present between the electrically conductive layer 250 and the patient's skin). In some implementations, the garment 110 can include a pocket or other similar structure including a metallic mesh that can be configured to act as an interface between the electrically conductive layer 250 and the patient's skin. In an example, the metallic mesh can include a knotted fabric having a silver coating. Upon deployment of the conductive gel, an electrical pathway can be defined between the electrically conductive layer 250 and the patient's skin.

As shown in FIG. 2A, therapy electrode can include a substrate 202 about which various components of the gel deployment device 201 can be arranged. The substrate 202 can include a plurality of conductive gel reservoirs 204 distributed about the surface of the substrate 202. For example, the conductive gel reservoirs 204 can be disposed about a first side of the substrate 202 (e.g., a top portion of the substrate 202 as depicted in the plan view of FIG. 2A and positioned opposite a bottom portion or side of the therapy electrode 200 that includes, for example, the conductive layer 250). Each of the conductive gel reservoirs 204 can be configured to hold a conductive gel. Depending upon the size of the conductive gel reservoirs, and the number of conductive gel reservoirs used, the amount of conductive gel contained within each conductive gel reservoir can be adjusted accordingly. For example, a gel deployment device 201 can include approximately 3-20 ml of conductive gel. In other examples, the gel deployment device 201 can be configured to hold between 5-15 ml of conductive gel. The conductive gel can be distributed amongst each of the conductive gel reservoirs 204. For example, each conductive gel reservoir 204 can be configured to hold approximately 0.5-5.0 ml of conductive gel. In other examples, each conductive gel reservoir can be configured to hold between 1.0 and 4.0 ml of conductive gel. In come implementations, depending upon the number and shape of the conductive gel reservoirs 204, additional quantities of conductive gel can be included in each conductive gel reservoir 204. For example, each conductive gel reservoir 204 can be configured to hold 6 ml of conductive gel, 7 ml of conductive gel, 8 ml of conductive gel, 9 ml of conductive gel, or 10 ml of conductive gel. As such, by varying the amount of total conductive gel held within each conductive gel reservoir 204, the total amount of gel contained within gel deployment device 201 can be adjusted.

In certain embodiments, the amount of conductive gel in each of the conductive gel reservoirs 204 can be equal or substantially equal such that the total amount of conductive gel is distributed among each of the conductive gel reservoirs 204. In other examples, the amount of conductive gel in each of the conductive gel reservoirs 204 can vary.

In certain implementations, gel deployment device 201 can include approximately 10 ml of conductive gel distributed substantially equally among each of the conductive gel reservoirs 204. As shown in the example gel deployment device 201 illustrated in FIG. 2A, with ten conductive gel reservoirs 204, each conductive gel reservoir 204 can be configured to hold approximately 0.5-1.5 ml of conductive gel. In some examples, each conductive gel reservoir 204 can be configured to hold approximately 1.0 ml of conductive gel. As noted above, in other examples, gel deployment device 201 can be configured to hold between approximately 3 ml and 20 ml of conductive gel. In such an example, each conductive gel reservoir 204 can be configured to hold approximately 0.3-2.0 ml of conductive gel. The amount of conductive gel can be determined based upon the number of reservoirs being used as well as the size of the electrically conductive layer the conductive gel is configured to be deployed on. For example, to provide an adequate amount of gel prior to delivering a therapeutic shock, a certain volume of gel per surface area of the therapy electrode can be delivered. In some examples, a ratio of between 0.3 and 2 ml of conductive gel per square inch of therapy electrode surface area can be used. In certain embodiments, a ratio of 1 ml per square inch of surface area can be used. As such, for a therapy electrode having a surface area of approximately 10 square inches, a gel deployment device can include 10 ml of conductive gel. In some implementations, the amount of conductive gel in the gel deployment device can also be based upon properties of the conductive gel itself. If the conductive gel has a low viscosity (e.g., a viscosity of about 100 mPa·s), a lower amount of the conductive gel can be used (e.g., 0.75 ml per square inch of surface area) as the conductive gel is more likely to flow along the surface of the therapy electrode as a faster pace than with a higher viscosity. Conversely, if the conductive gel has a higher viscosity (e.g., a viscosity of about 500 mPa·s), a larger amount of conductive gel can be used (e.g., 1.25 ml per square inch of surface area) as the conductive gel is more likely to flow along the surface of the therapy electrode at a slower pace.

Additionally, the therapy electrode 200 can also include a set of conductive gel reservoir protective caps 205. The protective caps 205 can be configured to cover the conductive gel reservoirs 204 to provide protection. In certain implementations, the protective caps 205 can be made from a hard plastic such as polystyrene or polycarbonate. The protective caps 205 can be sized (e.g., have a preconfigured thickness) such that the protective caps 205 provide a rigid outer structure for absorbing any accidental force or pressure exerted on the outside of the conductive gel reservoirs 204 prior to release of the conductive gel contained therein. In certain configurations, each of the conductive gel reservoirs 204 can have a single protective cap 205. In other implementations, the protective caps 205 can be sized to protect multiple conductive gel reservoirs 204.

As shown in FIG. 2B, each of the conductive gel reservoirs 204 can also be positioned around an adhesive seal 210, such as a ring-shaped adhesive seal. The adhesive seal 210 can be positioned such that it can prevent release of the conductive gel to a gel delivery outlet or exit port 212.

Referring again to FIG. 2A, the therapy electrode 200 can further include a pressure source 206 connected to a fluid channel 208. Examples of various pressure sources can be found in, for example, U.S. patent application Ser. No. 15/072,590 filed Mar. 17, 2016 and entitled "Systems and Methods for Conductive Gel Deployment," the content of which is incorporated herein by reference in its entirety. A copy of U.S. patent application Ser. No. 15/072,590 is included herein as Appendix A.

The pressure source 206, when activated by an activation signal, can release a pressurized fluid, such as a compressed gas, into the fluid channel 208. The fluid channel 208 can include a foam such as melamine foam positioned and configured to define a fluid passage between the pressure source 206 and each of the conductive gel reservoirs 204.

The hydraulic pressure of the fluid from the activated fluid pressure source 206 in the fluid channel 208 can result in a pressure being exerted on each of the conductive gel reservoirs 204. The pressure exerted on each of the conductive gel reservoirs 204 can result in the eventual rupturing of each adhesive seal 210 at or about substantially at the predetermined pressure level configured to rupture the adhesive seal. More specifically, as a result of the shape of the conductive gel reservoirs 204, the pressure exerted by the pressure source 206 can form a distributed pressure about the perimeter of the adhesive seal 210. Thus, the adhesive seal 210 can be more likely to rupture at multiple points about the perimeter (or rupture in a continuous portion up to and including the full perimeter of the adhesive seal) at or about substantially at the predetermined pressure level configured to rupture the adhesive seal 210, thereby resulting in release of the conductive gel from the conductive gel reservoirs 204. Such a configuration can offer an advantage over a configuration involving an adhesive seal configured to rupture from pressure being applied at only a single point. For instance, multiple points of applied pressure to the adhesive seal 210 can improve a likelihood that the adhesive seal 210 will be subjected to pressures at or about the predetermined pressure level, thereby increasing the likelihood that each of the multiple points of applied pressure will rupture, providing more area for the conductive gel to flow out of the conductive gel reservoirs 204.

Upon release of the adhesive seal 210, the conductive gel stored in each of the plurality of conductive gel reservoirs 204 can flow out of the plurality of exit ports 212, through apertures formed in the electrically conductive layer, and onto the exposed surface of the electrically conductive layer proximate to the patient's skin. The apertures in the electrically conductive layer are configured to be substantially aligned with the plurality of exit ports 212 so that, when released, the electrically conductive gel is dispensed onto the exposed surface of the electrode portion that is disposed substantially proximate to the patient's body (e.g., the electrically conductive layer 250). In some implementations, the apertures in the electrically conductive layer can be offset from the plurality of exit ports 212, depending upon the shape and size of the conductive gel reservoirs 204 and the adhesive seals 210. Such a design can provide an advantage during assembly of the therapy electrode 200 as manufacturing tolerances can be increased as a result of the potential offset of the apertures and the exit ports 212.

FIG. 2B shows a cross-sectional view of a single donut-shaped conductive gel reservoir 204. As shown in FIG. 2B, each individual conductive gel reservoir 204 can have a donut-shape that defines an open center portion 214. As noted above, the adhesive seal 210 can be positioned in the center of the conductive gel reservoir 204 within the open center portion 214. Similarly, an exit port 212 can be positioned in the center of the adhesive seal 210. In certain implementations, upon release of the adhesive seal 210, the conductive gel contained within the conductive gel reservoir 204 can flow through the exit port 212. Additional detail related to the operation of therapy electrode 200 is provided below.

FIG. 2C illustrates an exploded view of the therapy electrode 200, showing the multiple layers included in the manufacturing process of the therapy electrode 200. In certain implementations, a set of layers as shown in FIG. 2C (e.g., layers 220, 230 and 240 as described in greater detail below) can be assembled to manufacture the gel deployment device 201. It should be noted that the details provided in FIG. 2C and explained herein, as well as the overall process discussed below, is provided by way of example only. For example, changes to the techniques and configurations described herein can be implemented without substantially deviating from the scope of the disclosure.

The multilayer assembly as shown in FIG. 2C can include an outer layer 220. The outer layer 220 can be formed from, for example, various polymers such as formed thermoplastic. In some implementations, the outer layer 220 can be constructed from an ethylene acid copolymer. In some examples, a copolymer having a low water vapor transmission rate can be chosen. For example, the outer layer 220 can be constructed from DuPont™ Surlyn®, which is an ionomer resin of ethylene acid copolymer. Such a resin can be processed in conventional blown film, cast film, sheet extrusion and coextrusion equipment designed to process polyethylene and ethylene copolymer type resins. The ionomer resin can be configured to have a relatively low water vapor transmission rate (e.g., approximately 0.8 g/100 in$^2$/day). For example, a material with a low permeability such as an ionomer resin can provide an advantage of a longer shelf-life of the conductive gel deployment device relative to conventional configurations as the rate of evaporation of the conductive gel through the ionomer resin is low. Thus, the conductive gel inside the conductive gel reservoirs (e.g., conductive gel reservoirs 204) can maintain its original viscosity when stored in the conductive gel reservoirs for an extended period of time (e.g., for a period of two or more years).

In some examples, the outer layer 220 can be manufactured from the ionomer resin using a vacuum forming machine. An appropriately sized sheet of the ionomer resin can be placed into the vacuum forming machine along with a mold or plate including a negative of the features to be formed on the outer layer 220. The sheet of the ionomer resin can be appropriately heated, stretched against the mold, and pressed against the mold by a vacuum pressure. After the pressure is released, the sheet of ionomer resin has been molded into the outer layer 220. Based upon the resulting desired characteristics of the outer layer 220, the physical properties of the ionomer resin sheet can be chosen or adjusted accordingly. For example, the thickness of the ionomer resin sheet can be selected based upon the desired flexibility of the finished outer layer 220 as well as the pressures that will be exerted on the outer layer 220. In some examples, the thickness of the ionomer resin sheet can be between 0.0095-0.0120 inches thick. In certain implementations, the thickness of the ionomer resin sheet can be 0.011 inches thick. Additional characteristics such as resin density and other related properties can also be determined based upon resulting desired characteristics of the finished outer layer 220.

The outer layer 220 can include multiple gel reservoir top portions 222. The gel reservoir top portions 222 can be formed to provide an air pocket as well as to provide a surface against which a pressurized fluid can exert a pressure when applied to a conductive gel reservoir 204. Similarly, the outer layer 220 can include a pressure source top portion 224. The pressure source top portion 224 can be arranged to define a cavity for insertion and containment of, for example, pressure source 206.

Additionally, the outer layer 220 can include one or more ventilation holes 226. When worn by a patient, the therapy electrode 200 is substantially held against the patient's skin (or, depending upon the type of garment 110 being worn, a layer of the garment 110 can be positioned between the therapy electrode 200 and the patient's skin). By including the ventilation holes 226 (in combination with ventilation holes 234, 242 and 254 described below in additional detail), increased air flow can be provided to a patient's skin, thereby reducing potential discomfort or skin irritation.

The multilayer assembly as shown in FIG. 2C can also include a diaphragm layer 230. Like the outer layer 220, the diaphragm layer 230 can be formed from, for example, an ionomer resin. As before, a vacuum forming process can be used to form a sheet of the ionomer resin into the diaphragm layer 230. An appropriately sized sheet of the ionomer resin can be placed into the vacuum forming machine along with a mold or plate including a negative of the features to be formed on the diaphragm layer 230. The sheet of the ionomer resin can be appropriately heated, stretched against the mold, and pressed against the mold by a vacuum pressure. After the pressure is released, the sheet of ionomer resin has been molded into the diaphragm layer 230. Based upon the resulting desired characteristics of the diaphragm layer 230, the physical properties of the ionomer resin sheet can be chosen or adjusted accordingly. For example, the thickness of the ionomer resin sheet can be selected based upon the desired flexibility of the finished diaphragm layer 230. In some examples, the thickness of the ionomer resin sheet can be between 0.0095-0.0120 inches thick. In certain implementations, the thickness of the ionomer resin sheet can be 0.011 inches thick. Additional characteristics such as resin density and other related properties can also be determined based upon resulting desired characteristics of the finished diaphragm layer 230.

The diaphragm layer 230 can also include multiple gel reservoir inner portions 232. The gel reservoir inner portions 232 can be formed such that, upon layering of the outer layer 220 and the diaphragm layer 230, a small air gap is defined between each gel reservoir top portion 222 and a corresponding gel reservoir inner portion 232. As such, the gel reservoir inner portions 232 can be sized slightly smaller than the gel reservoir top portions 222. This size difference allows the smaller gel reservoir inner portions 232 to nest within the gel reservoir top portions 222 and define the air gap there-between. With such an arrangement of components, upon application of an exerted pressure from a pressurized fluid, pressure within the air gap can increase until an adjacent adhesive seal ruptures. When the adhesive seal ruptures, the exerted pressure can deform the gel reservoir inner portion 232, thereby causing flow of the conductive gel contained within that conductive gel reservoir 204. Additionally, the second layer 230 can include one or more ventilation holes 234 in alignment with ventilation holes 226.

The multilayer assembly as shown in FIG. 2C can further include a lidding layer 240. The lidding layer 240 is configured to adhere to the diaphragm layer 230 to provide a sealing surface for holding the conductive gel within gel reservoir inner portions 232 of the diaphragm layer 230. The lidding layer 240 can be formed from, for example, a polyester film that includes a heat sealable adhesive layer. In some examples, Scotchpak™ MA250M Medical Adhesion Film can be used for the construction of the lidding layer 240. Similar to the ionomer resin sheet as described above, the thickness of the polyester film can be selected based upon the desired flexibility of the finished lidding layer 240. In some examples, the thickness of the ionomer resin sheet can be between 0.00230-0.00260 inches thick. In certain implementations, the thickness of the ionomer resin sheet can be 0.00245 inches thick. Additionally, like the ionomer resin as described above, a polyester film with a low permeability and water vapor transmission rate can be selected. Additional characteristics such as adhesive density and other related properties can also be determined based upon resulting desired characteristics of the finished lidding layer 240.

As described above, the lidding layer 240 can be configured to act as barrier layer preventing unwanted release of the conductive gel from the conductive gel reservoirs 204. As such, the adhesive seals 210 can be configured and positioned between the diaphragm layer 230 and the lidding layer 240. Additional detail regarding adhesive seals, and their incorporation and positioning in a gel deployment device, is provided in the discussion of FIGS. 3A-3D provided below.

Similarly, the lidding layer 240 includes exit ports 212 (as shown in FIG. 2B) positioned adjacent to (or, if a ring-shaped adhesive seal is used, in the center of) the adhesive seals 210. Additionally, the lidding layer 240 can include one or more ventilation holes 242 in alignment with ventilation holes 226 and ventilation holes 234 as described above.

When manufactured, the outer layer 220, the diaphragm layer 230 and the lidding layer 240 can be combined into a multilayer gel deployment device 201. As noted above, the gel deployment device 201 can be configured to deploy an amount of conductive gel prior to application of, for example, a therapeutic shock.

As noted above, a therapy electrode 200 can also include an electrically conductive layer 250. The electrically conductive layer 250 can be formed from a conductive material such as metal foil or another thin, pliable conductive material. For example, the electrically conductive layer 250 can be constructed from rolled stainless steel. In some examples, the thickness of the electrically conductive layer 250 can be between 0.00295-0.00305 inches thick. In certain implementations, the thickness of the electrically conductive layer 250 can be approximately 0.003 inches thick.

The electrically conductive layer 250 can be configured to be positioned substantially proximate to the patient's skin and to direct a therapeutic shock towards the patient's skin. Depending upon the design, the electrically conductive layer 250 can also be integrated directly into the garment, e.g., garment 110 as described above. In certain implementations, the electrically conductive layer 250 is positioned and configured to work in concert with gel deployment device 201. This provides for a replaceable gel deployment device 201 that can be replaced without replacing the electrically conductive layer 250 as well. An example of a garment including an integrated electrically conductive layer and a replaceable gel deployment device is described in detail in U.S. Pat. No. 9,008,801 issued Apr. 14, 2015 and entitled "Wearable Therapeutic Device," the content of which is incorporated herein by reference.

Additionally, the electrically conductive layer 250 can include a series of apertures 252. The apertures 252 can be arranged in a similar geometry as the placement of the adhesive seals 210 and the exit ports 212 (as shown, for example, in FIG. 2B). Such an arrangement of components provides for conductive gel flow through the exit ports 212 and then through the apertures 252 in the electrically conductive layer 250 and onto a patient's skin.

When applying a therapeutic shock, the electrical current typically moves to the edges of the conductive material prior to arcing to the patient's skin. When the current collects at the edge prior to arcing to the patient's skin, more current is applied to a single area of the patient's skin, which can result in tissue damage to the patient's skin (e.g., a burn or other similar skin irritation). In order to better balance the electrical current delivered to the patient (e.g., to allow for substantially even distribution of the current through the electrode-patient interface), the electrically conductive layer 250 can include one or more openings, e.g., opening 254. For example, the opening 254 can define an additional edge for better distributing the electrical current. Thus, as shown in FIG. 2C, the electrically conductive layer 250 includes an outer edge 256 designed by the overall shape of the therapy electrode, as well as an inner edge 258 defined by the opening 254. The combination of both the outer edge 256 and the inner edge 258 combine to increase an overall edge length of the electrically conductive layer 250. In some examples, the opening 254 can be configured to substantially align with at least a portion of the ventilation holes 226, ventilation holes 234, and ventilation holes 242 to facilitate air flow to the patient's skin adjacent to the therapy electrode 200. However, other configurations are possible, including ventilation holes 226, 234 and 242 being disposed at locations other than in alignment with the opening 254.

By providing ventilation to the patient's skin (e.g., via the combination of ventilation holes 226, 234, 242 and the opening 254), the therapy electrode 200 can provide several advantages over conventional designs. For example, increased air flow can reduce the likelihood that a patient will experience discomfort due to sweating as a result of the therapy electrode 200 being pressed against their skin. The increased airflow can cool the skin covered by the therapy electrode 200 as well as facilitate evaporation of any sweat that is produced by the skin covered by the therapy electrode 200.

The electrically conductive layer 250 as shown in FIG. 2C is shown by way of example only. As noted above, by increasing the total edge length of the electrically conductive layer 250, the electrical current can be more evenly distributed to the patient. As such, the electrically conductive layer 250 can include additional holes having preconfigured shapes (e.g., a star, a flower, a diamond, or any arbitrary shape) to increase the total edge length. Similarly, the outer edge 256 can include a preconfigured design such as a scalloped edge or any arbitrarily shaped edge rather than being, for example, cut straight, thereby also increasing the total edge length.

Similarly, it should be noted that the number, shape, and position of the ventilation holes 226, 234 and 242 are shown by way of example only. Depending upon the layout of the conductive gel reservoirs 204, the number, shape, and position of the ventilation holes can be altered accordingly.

As noted above, each of the lidding layer 240 and the electrically conductive layer 250 includes one or more exit ports in the lidding layer 240 (e.g., exit ports 212 as shown in FIG. 2B) and apertures 252 in the electrically conductive layer 250 positioned such that the exit ports and apertures 252 are aligned with the open center portion (e.g., open center portion 214 as shown in FIG. 2B) of each conductive gel reservoir 204. Depending upon the manufacturing process, the exit ports 212 and apertures 252 can be formed in the lidding layer 240 and the electrically conductive layer 250 prior to or during assembly of the multilayer device illustrated in FIG. 2C. In traditional manufacturing processes, the adhesive seals are positioned adjacent to the conductive gel reservoirs during an assembly process. However, this step can require precise position of the therapy electrode to properly position the adhesive seals with the conductive gel reservoirs. Using the designs and techniques as described herein, for example, the open center portion 214 of the conductive gel reservoirs can be used to align a piercing device configured to pierce the multilayered device to produce the exit ports 212 and the apertures 252 during manufacture, thereby increasing the manufacturing tolerances of the therapy electrode 200 as the piercing device can be configured to adjust to the positions of the open center portions 214. However, if such a process is used, for example, to stamp out the exit ports 212 and the apertures 252 after assembly of the multilayered assembly, a sealant or adhesive plug (not shown in FIG. 2C) can be applied to the outer layer 220 to prevent unwanted fluid flow upon release of the conductive gel.

In an example manufacturing process, each layer as shown in FIG. 2C can be configured to be adhered to its adjacent layers via an adhesion process. For example, each of the outer layer 220 and the diaphragm layer 230 can be bonded together directly. Heat and pressure can be applied to each of the outer layer 220 and the diaphragm layer 230 to, e.g., chemically bond the two layers together. As noted above, the lidding layer 240 can be manufactured from a polyester film that includes a heat-activated adhesive. In certain implementations, the diaphragm layer 230 (or the combined top layer 220 and diaphragm layer 230) can be positioned on top of the lidding layer 240 such that the lidding layer 240 acts to seal the conductive gel in the gel reservoir inner portions 232 of the diaphragm layer 230. Heat can be applied to the stacked structure, thereby forming the multilayer gel deployment device as described above. Additionally, an amount of heat-activated adhesive (or another similar adhesive) can be applied between the lidding layer 240 and the electrically conductive layer 250. The electrically conductive layer 250 can then be adhered to the lidding layer 240 (and, subsequently, the multilayered gel deployment device), thereby resulting in a complete therapy electrode 200.

In operation, the therapy electrode 200 as describe above can be configured to provide a therapeutic shock to a patient current experiencing, for example, a cardiac arrhythmia. Prior to delivering the shock, the conductive gel deployment device 201 associated with the therapy electrode 200 can be configured to deploy the conductive gel onto the patient's skin. Initially, the pressure source 206 can be triggered to produce an increased fluid pressure in the fluid channel 208. The increased fluid pressure can cause internal pressure within the air gaps between each gel reservoir top portion 222 and its adjacent gel reservoir inner portion 232 to increase. As the internal pressure within the conductive gel reservoirs 204 increases, a distributed pressure can be applied about the perimeter of each of the adhesive seals 210. After the distributed pressure reaches a high enough level (e.g., 8-22 psi), each individual adhesive seal 210 can begin to rupture, causing the release of the conductive gel from each of the conductive gel reservoirs 204. Pressure within each of the conductive gel reservoirs 204 can cause deformation of the gel reservoir inner portion 232, which results in the conductive gel being pushed out of the conductive gel reservoirs 204. The conductive gel can flow through the exit ports 212 and can be distributed on the electrically conductive surface 250 and the patient's skin. After gel deployment, the electrically conductive surface 250 can direct the therapeutic shock through the conductive gel, which conducts the therapeutic shock to the patient's skin.

Figure 3A:
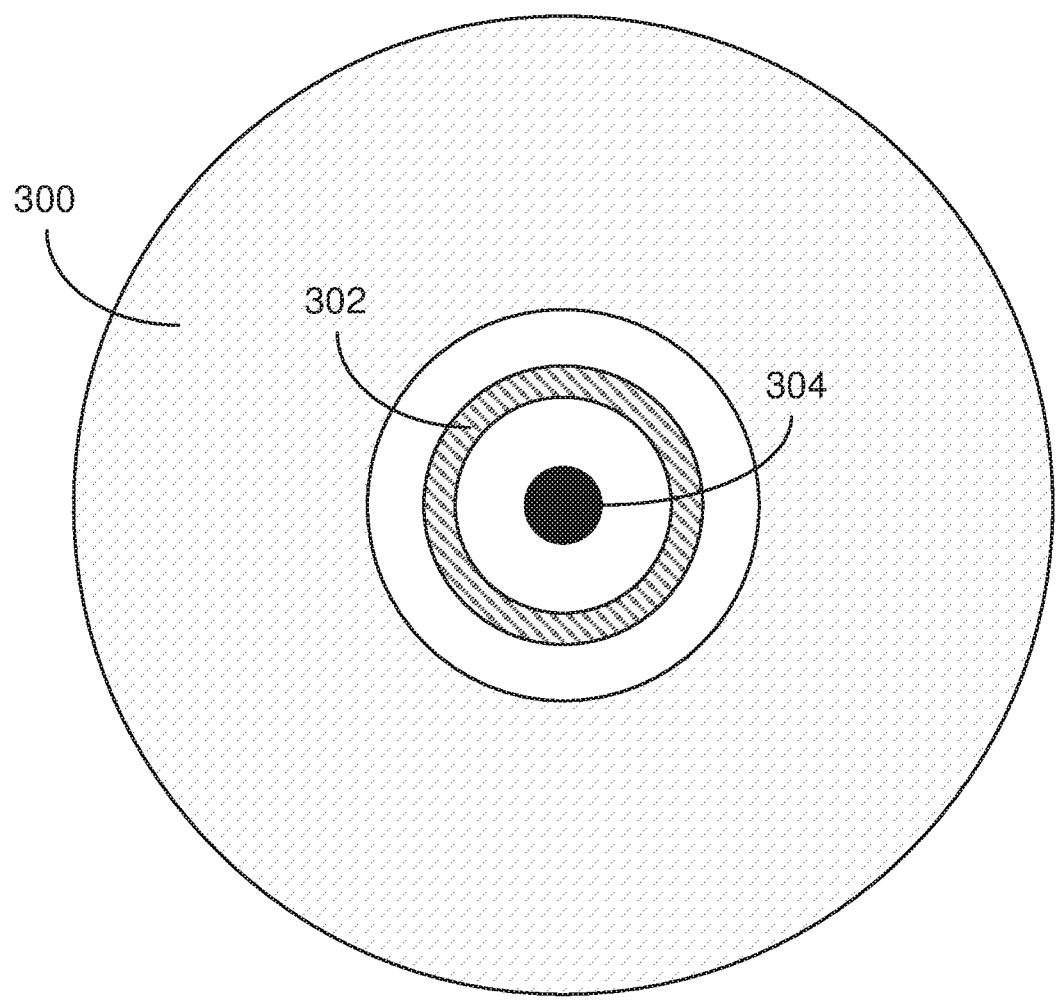
FIGS. 3A-3D depict a conductive gel reservoir and adhesive seal assembly, in accordance with an example of the present disclosure.

FIGS. 3A-3D illustrate a detailed view of a conductive gel reservoir and an adhesive seal, as well as provide additional detail regarding how an adhesive seal ruptures and the resulting conductive gel flow through the ruptured adhesive seal to an exit port. FIG. 3A shows a close-up view of conductive gel reservoir 300. In certain embodiments, the conductive gel reservoir 300 can have, for example a donut shape. Similar to the discussion of FIG. 2B above, the conductive gel reservoir can surround an adhesive seal 302. The adhesive seal 302 can be positioned and configured such that it prevents flow of conductive gel from the conductive gel reservoir 300 to an exit port 304.

Figure 3B:
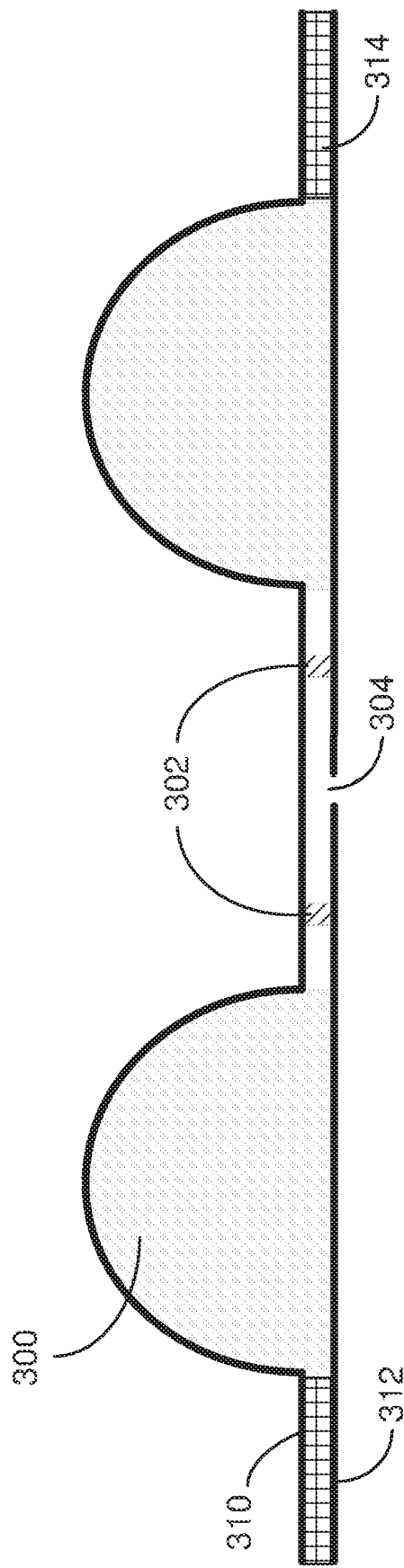

The adhesive seal 302 can be positioned or inserted between the diaphragm layer and the lidding layer. FIG. 3B shows a cross-sectional view of a portion of a gel deployment device. In particular, FIG. 3B shows the diaphragm layer 310 and the lidding layer 312. As described above, in order to adhere the diaphragm layer 310 and the lidding layer 312, a certain amount of heat can be applied to the two layers. The diaphragm layer 310 and the lidding layer 312 can then be pressed together using a certain force. By altering the temperature and the force, the peeling strength of the assembled layers (e.g., a pressure level at which the diaphragm layer 310 and the lidding layer 312 will pull apart) can be configured for an intended purpose. For example, to securely fasten the lidding layer 312 to the diaphragm layer 310 for prevention of conductive gel leakage from the conductive gel reservoirs 300, the layers can be bonded at area 314 at approximately 300° F. with a pressing force of approximately 10 N for about 3 seconds. Such a bonding can have, for example, a peeling strength of 100 psi.

In certain embodiments, the adhesive seal 302 can be formed to have a lower peeling strength than area 314. For example, in order to cause the adhesive seal 302 to rupture in response to an applied pressure of approximately 8-22 psi (as described above), the adhesive seal 302 can be configured to have a peeling strength of approximately 10 psi. To form such an adhesive seal 302, a lower temperature and force can be used when forming the adhesive seal 302 between the diaphragm layer 310 and the lidding layer 312. For example, the diaphragm layer 310 and the lidding layer 312 can be bonded at approximately 300° F. with a pressing force of approximately 7.5 N for about 3 seconds to form the adhesive seal 302. By providing a lower peeling strength for the adhesive seal 302 relative to layer bonding area 314, the adhesive seal 302 is configured to rupture at a lower pressure (e.g., 8-22 psi), thereby facilitating release of the conductive gel from the conductive gel reservoir 300 to the exit port 304. Additionally, the thickness (e.g., the difference between the outer diameter minus the inner diameter) of the adhesive seal 302 can be configured to provide a particular peeling strength. For example, the adhesive seal 302 can have a thickness of approximately 0.0005-0.004 inches thick. In certain implementations, the adhesive seal 302 can have a thickness of approximately 0.001 inches thick.

As described herein, the adhesive seal 302 is thus a particular area of adhesion between the diaphragm layer 310 and the lidding layer 312 that has a configured peeling strength. However, such an adhesive seal 302 is provided by way of example only. In certain embodiments, the seal 302 can include an additional component inserted between the diaphragm layer 310 and the lidding layer 312. For example, the seal 302 can include a rubber (or other similar material such as a flexible foam) O-ring positioned between the diaphragm layer 310 and the lidding layer 312 and secured (e.g., via a rubber adhesive) between the diaphragm layer 310 and the lidding layer 312 to provide a configured peeling strength between the layers.

Figure 3C:
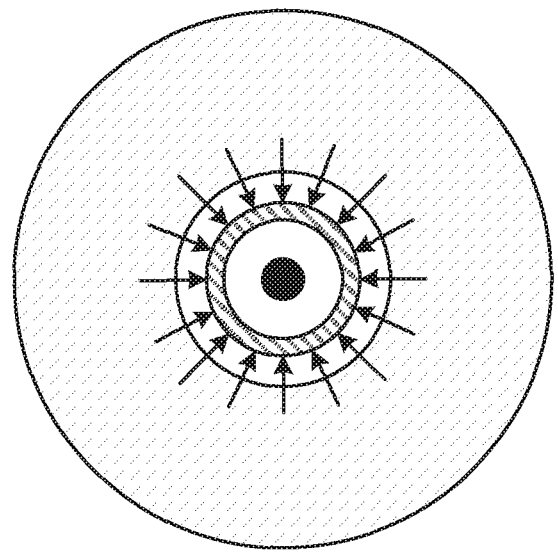
Figure 3D:
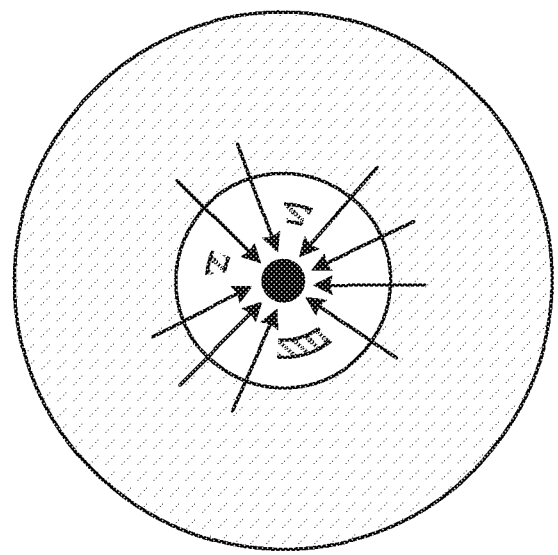

FIGS. 3C and 3D illustrate an example of applied pressure to an adhesive seal (FIG. 3C) and a ruptured adhesive seal and resulting conductive gel flow (FIG. 3D). As shown in FIG. 3C, when a pressure (e.g., from a pressurized fluid) is applied to a conductive gel reservoir, the pressure is evenly or substantially even distributed about the perimeter of the adhesive seal, as is indicated by the arrows in FIG. 3C. It should be noted that, though the arrows in FIG. 3C indicate pressure being applied at a number of points about the adhesive seal, this is provided by way of example only and, in actual practice, the pressure is applied evenly or substantially evenly about the perimeter of the adhesive seal. As the applied pressure reaches a level that results in rupturing of the adhesive seal (e.g., 8-22 psi as described above), the adhesive seal can rupture at one or more points about the perimeter of the adhesive seal. For example, a continuous portion of the adhesive seal (up to an including the full perimeter of the adhesive seal) can rupture substantially simultaneously, resulting in release of the conductive gel about the full length of the continuous portion that has ruptured. Similarly, multiple points about the perimeter of the adhesive seal can rupture, thereby resulting in a fluid path for release of the conductive gel at each of the multiple rupture points.

As shown in FIG. 3D, for example, various portions of the adhesive seal have failed. As indicated by the arrows in FIG. 3D, the conductive fluid can flow through the ruptured portions of the adhesive seal and to the exit port. As noted above, the pressure applied to the conductive gel reservoir (that resulting in the rupturing of the adhesive seal) also acts to push the conductive gel out of the conductive gel reservoir, through the ruptured portions of the adhesive seal and to the exit port. It should be noted that, though the arrows in FIG. 3D indicate a limited number of conductive gel paths for flowing through the ruptured adhesive seal, this is provided by way of example only and, in actual practice, the conductive gel would flow from the conductive gel reservoir to the exit port through any portion of the adhesive seal that has ruptured at a rate determined by the pressure applied to the conductive gel reservoir.

Figure 4A:
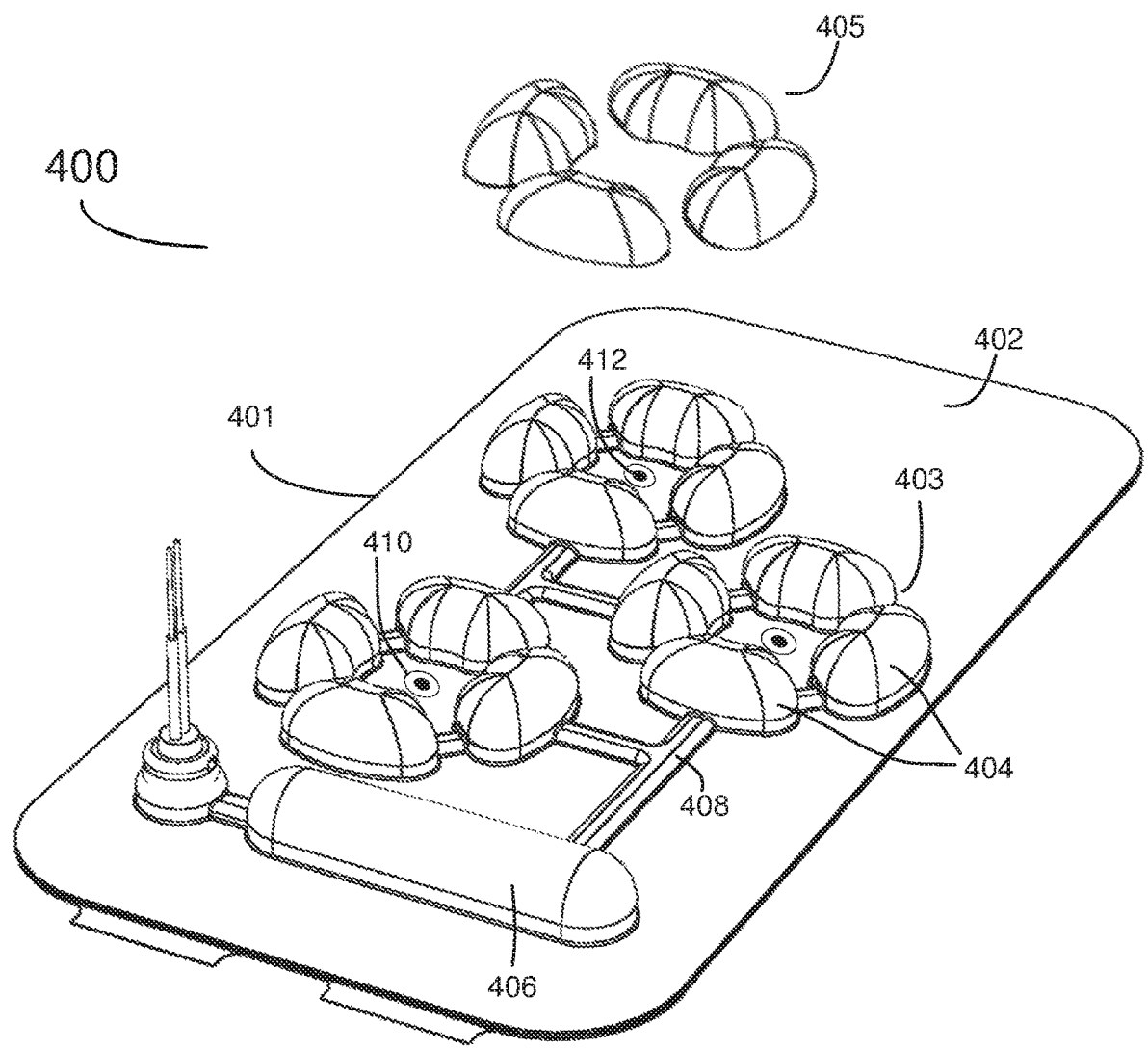
FIG. 4A depicts a plan view of a therapy electrode, in accordance with an example of the present disclosure.
Figure 4B:
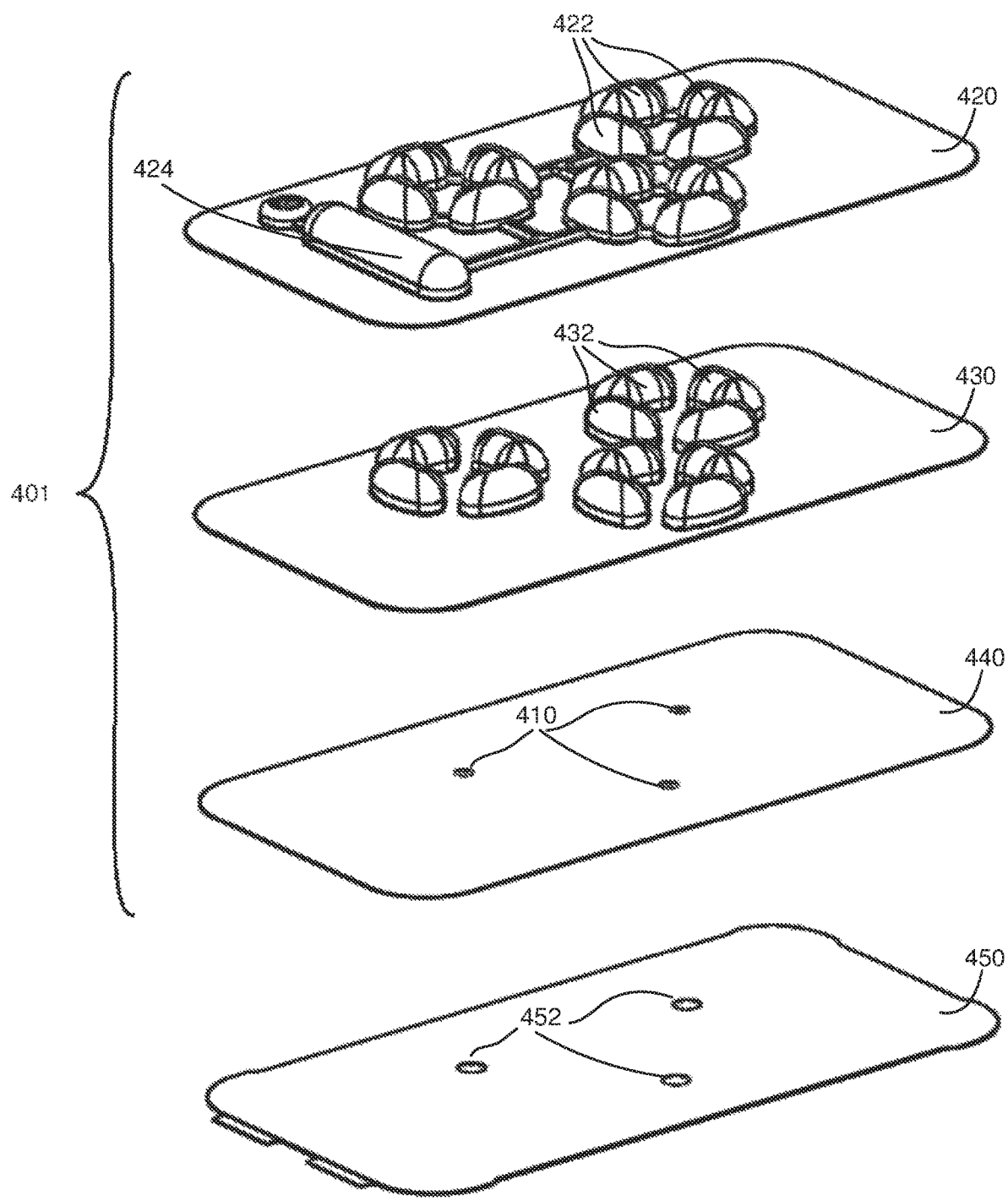
FIG. 4B depicts an exploded view of the therapy electrode of FIG. 3A.

FIGS. 4A and 4B illustrate a conductive gel deployment device that uses reservoir clusters on the conductive gel deployment device. This configuration places a ring-shaped adhesive seal in the center of a cluster of individual conductive gel reservoirs such that multiple conductive gel reservoirs can be arranged about a single adhesive seal. Upon application of a pressure to the conductive gel reservoirs, a distributed pressure is exerted about a perimeter of the adhesive seals. In such an example, the adhesive seal can rupture in a variety of ways. For example, a continuous portion of the adhesive seal (up to an including the full perimeter of the adhesive seal) can rupture substantially simultaneously, resulting in release of the conductive gel about the full length of the continuous portion that has ruptured. Similarly, multiple points about the perimeter of the adhesive seal can rupture, thereby resulting in a fluid path for release of the conductive gel at each of the multiple rupture points.

FIG. 4A is a plan view of a therapy electrode 400 that includes a conductive gel deployment device 401 using, for example in this configuration, reservoirs clusters. Like therapy electrode 200, the therapy electrode 400 can be a multiple layer laminated structure that includes an electrically conductive layer 450 (shown in FIG. 4B and explained in greater detail below). In use, the electrically conductive layer 450 can be disposed proximate to the patient's skin, although the conductive layer need not make direct contact with the patient (e.g., in implementations where conductive portions of the garment 110 act as an interface between the conductive layer 450 and the patient's skin, and/or implementations where portions of the patient's clothing may be present between the electrically conductive layer 450 and the patient's skin). In some implementations, the garment 110 can include a pocket or other similar structure including a metallic mesh that can be configured to act as an interface between the electrically conductive layer 450 and the patient's skin. In an example, the metallic mesh can include a knotted fabric having a silver coating. Upon deployment of the conductive gel, an electrical pathway can be defined between the electrically conductive layer 450 and the patient's skin.

As shown in FIG. 4A, therapy electrode can include a substrate 402 about which various components of the gel deployment device 401 can be arranged. The substrate 402 can include a plurality of reservoir clusters 403 distributed about the surface of the substrate 402. Each of the reservoir clusters 403 can include multiple conductive gel reservoirs 404. For example, as shown in FIG. 4A, each conductive gel cluster 403 includes four conductive gel reservoirs 404 arranged about a center point, thereby defining an open center position. In certain implementations, the gel clusters 403 can be disposed about a first side of the substrate 402 (e.g., a top portion of the substrate 402 as depicted in the plan view of FIG. 4A and positioned opposite a bottom portion or side of the therapy electrode 400 that includes, for example, the conductive layer 450). Each of the conductive gel reservoirs 404 can be configured to hold a volume of conductive gel. Depending upon the total number of conductive gel reservoirs 404 used for each reservoir cluster 403, and the total number of reservoir clusters 403 used, the amount of conductive gel contained within each conductive gel reservoir 404 can be adjusted accordingly. For example, the gel deployment device 401 can include approximately 3-20 ml of conductive gel. In other examples, the gel deployment device 401 can be configured to hold between 5-15 ml of conductive gel. The conductive gel can be distributed amongst each of the conductive gel reservoirs 404. For example, each conductive gel reservoir 404 can be configured to hold approximately 0.5-5.0 ml of conductive gel. In other examples, each conductive gel reservoir 404 can be configured to hold between 1.0 and 4.0 ml of conductive gel. In come implementations, depending upon the number and shape of the conductive gel reservoirs 404, additional quantities of conductive gel can be included in each conductive gel reservoir 404. For example, each conductive gel reservoir 404 can be configured to hold 6 ml of conductive gel, 7 ml of conductive gel, 8 ml of conductive gel, 9 ml of conductive gel, or 10 ml of conductive gel. As such, by varying the amount of total conductive gel held within each conductive gel reservoir 404, the total amount of gel contained within gel deployment device 401 can be adjusted.

In certain embodiments, the amount of conductive gel in each of the conductive gel reservoirs 404 can be equal or substantially equal such that the total amount of conductive gel is distributed among each of the conductive gel reservoirs 404. In other examples, the amount of conductive gel in each of the conductive gel reservoirs 404 can vary.

In certain implementations, the gel deployment device 401 can be configured to hold approximately 10 ml of the conductive gel distributed substantially equally among each of the conductive gel reservoirs 404. As shown in the example gel deployment device illustrated in FIG. 4A, with twelve conductive gel reservoirs 404, each conductive gel reservoir 404 can be configured to hold approximately 0.85 ml of conductive gel. As noted above, in other examples, a gel deployment device can be configured to hold between approximately 3 ml and 20 ml of conductive gel. The amount of conductive gel can be determined based upon the number of reservoirs being used as well as the size of the electrically conductive layer the conductive gel is configured to be deployed on. In certain embodiments, the amount of conductive gel in each of the conductive gel reservoirs can be equal or substantially equal such that the total amount of conductive gel is distributed among each of the conductive gel reservoirs.

Additionally, the therapy electrode 400 can also include a set of conductive gel reservoir protective caps 405. The protective caps 405 can be configured to cover the conductive gel reservoirs 404 to provide protection. In certain implementations, the protective caps 405 can be made from a hard plastic such as polystyrene or polycarbonate. The protective caps 405 can be sized (e.g., have a preconfigured thickness) such that the protective caps 405 provide a rigid outer structure for absorbing any accidental force or pressure exerted on the outside of the conductive gel reservoirs 404 prior to release of the conductive gel contained therein. In certain configurations, each of the conductive gel reservoirs 404 can have a single protective cap 405. In other implementations, the protective caps 405 can be sized to protect multiple conductive gel reservoirs 404. For example, a single protective cap 405 can be sized to cover a reservoir cluster 403.

Each of the reservoir clusters 403 can be positioned around an adhesive seal 410, such as a ring-shaped adhesive seal. The adhesive seal 410 can be positioned such that it can prevent release of the conductive gel to a gel delivery outlet or exit port 412.

The therapy electrode 400 can further include a pressure source 406 connected to a fluid channel 408. The pressure source 406, when activated by an activation signal, can release a fluid, such as compressed gas, into the fluid channel 408. The fluid channel 408 can include a foam such as melamine foam positioned and configured to define a fluid passageway between the pressure source 406 and each of the conductive gel reservoirs 404.

The hydraulic pressure of the fluid from the activated fluid pressure source 406 in the fluid channel 408 can result in a pressure being exerted on each of the conductive gel reservoirs 404. The pressure exerted on each of the conductive gel reservoirs 404 can result in the eventual rupturing of each adhesive seal 410 at or about substantially at the predetermined pressure level configured to rupture the adhesive seal 410. In certain implementations, as a result of the shape of the conductive gel reservoirs 404 and their positioning within the reservoir cluster 403, the pressure exerted by the pressure source 406 can form a distributed pressure about the perimeter of the adhesive seal 410. Thus, the adhesive seal 410 can be more likely to rupture at multiple points about the perimeter (or in a continuous portion up to and including the full perimeter of the adhesive seal 410), at or about substantially at the predetermined pressure level configured to rupture the adhesive seal 410, thereby resulting in release of the conductive gel from each reservoir cluster 403. Such a configuration can offer an advantage over a configuration involving an adhesive seal configured to rupture from pressure being applied at only a single point. For instance, multiple points of applied pressure to the adhesive seal 410 can improve a likelihood that the adhesive seal 410 will be subjected to pressures at or about the predetermined pressure level, thereby increasing the likelihood that each of the multiple points of applied pressure will rupture, providing more area for the conductive gel to flow out of the conductive gel reservoirs 404.

Upon release of the adhesive seal 410, the conductive gel stored in each of the plurality of conductive gel reservoirs 404 in a respective reservoir cluster 403 can flow out of the plurality of exit ports 412. The conductive gel then can flow through apertures formed in the electrically conductive layer 450 and onto the exposed surface of the electrically conductive layer 450 proximate to the patient's skin. The apertures in the electrically conductive layer 450 are configured to be substantially aligned with the plurality of exit ports 412 so that, when released, the electrically conductive gel is dispensed onto the exposed surface of the electrode portion that is disposed substantially proximate to the patient's body. In some implementations, the apertures in the electrically conductive layer can be offset from the plurality of exit ports 412, depending upon the shape and size of the conductive gel reservoirs 404, the arrangement of the reservoir clusters 403, and the adjacent adhesive seals 410. Such a design can provide an advantage during assembly of the therapy electrode 400 as manufacturing tolerances can be increased as a result of the potential offset of the apertures and the exit ports.

FIG. 4B illustrates an exploded view of the therapy electrode 400, showing the multiple layers included in the manufacturing process of the therapy electrode 400. In certain implementations, a set of layers as shown in FIG. 4B (e.g., layers 420, 430 and 440 as described in greater detail below) can be assembled to manufacture the gel deployment device 401. It should be noted that the details provided in FIG. 4B and explained herein, as well as the overall process discussed below, is provided by way of example only. For example, changes to the techniques and configurations described herein can be implemented without substantially deviating from the scope of the disclosure.

The multilayer assembly as shown in FIG. 4B can include an outer layer 420. The outer layer 420 can be formed from, for example, various polymers such as formed thermoplastic. In some implementations, the outer layer 420 can be constructed from an ethylene acid copolymer. In some examples, a copolymer having a low water vapor transmission rate can be chosen. For example, the outer layer 420 can be constructed from an ionomer resin of ethylene acid copolymer such as DuPont™ Surlyn® as described above. Such a resin can be processed in conventional blown film, cast film, sheet extrusion and coextrusion equipment designed to process polyethylene and ethylene copolymer type resins. The ionomer resin can be configured to have a relatively low water vapor transmission rate (e.g., approximately 0.8 g/100 in$^2$/day). For example, a material with a low permeability such as an ionomer resin can provide an advantage of a longer shelf-life of the conductive gel deployment device relative to conventional configurations as the rate of evaporation of the conductive gel through the ionomer resin is low. Thus, the conductive gel inside the conductive gel reservoirs (e.g., conductive gel reservoirs 404) can maintain its original viscosity when stored in the conductive gel reservoirs for an extended period of time (e.g., for a period of two or more years).

In some examples, the outer layer 420 can be manufactured from the ionomer resin using a vacuum forming machine. A vacuum forming process can be used to form a sheet of the ionomer resin into the outer layer 420. An appropriately sized sheet of the ionomer resin can be placed into the vacuum forming machine along with a mold or plate including a negative of the features to be formed on the outer layer 420. The sheet of the ionomer resin can be appropriately heated, stretched against the mold, and pressed against the mold by a vacuum pressure. After the pressure is released, the sheet of ionomer resin has been molded into the outer layer 420. Based upon the resulting desired characteristics of the outer layer 420, the physical properties of the ionomer resin sheet can be chosen or adjusted accordingly. For example, the thickness of the ionomer resin sheet can be selected based upon the desired flexibility of the finished outer layer 420 as well as the pressures that will be exerted on the outer layer 420. In some examples, the thickness of the ionomer resin sheet can be between 0.0095-0.0120 inches thick. In certain implementations, the thickness of the ionomer resin sheet can be 0.011 inches thick. Additional characteristics such as resin density and other related properties can also be determined based upon resulting desired characteristics of the finished outer layer 420.

The outer layer 420 can include multiple gel reservoir top portions 422. The gel reservoir top portions 422 can be formed to provide an air pocket as well as a surface against which a pressurized fluid can exert a pressure when applied to a conductive gel reservoir 404. Similarly, the outer layer 420 can include a pressure source top portion 424. The pressure source top portion 424 can be arranged to define a cavity for insertion and containment of, for example, pressure source 406.

The multilayer assembly as shown in FIG. 4B can also include a diaphragm layer 430. Like the outer layer 420, the diaphragm layer 430 can be formed from, for example, an ionomer resin. As before, a vacuum forming process can be used to form a sheet of the ionomer resin into the diaphragm layer 430. An appropriately sized sheet of the ionomer resin can be placed into the vacuum forming machine along with a mold or plate including a negative of the features to be formed on the diaphragm layer 430. The sheet of the ionomer resin can be appropriately heated, stretched against the mold, and pressed against the mold by a vacuum pressure. After the pressure is released, the sheet of ionomer resin has been molded into the diaphragm layer 430. Based upon the resulting desired characteristics of the diaphragm layer 430, the physical properties of the ionomer resin sheet can be chosen or adjusted accordingly. For example, the thickness of the ionomer resin sheet can be selected based upon the desired flexibility of the finished diaphragm layer 430. In some examples, the thickness of the ionomer resin sheet can be between 0.0095-0.0120 inches thick. In certain implementations, the thickness of the ionomer resin sheet can be 0.011 inches thick. Additional characteristics such as resin density and other related properties can also be determined based upon resulting desired characteristics of the finished diaphragm layer 430.

The diaphragm layer 430 can also include multiple gel reservoir inner portions 432. The gel reservoir inner portions 432 can be formed such that, upon layering of the outer layer 420 and the diaphragm layer 430, a small air gap is defined between each gel reservoir top portion 422 and a corresponding gel reservoir inner portion 432. As such, the gel reservoir inner portions 432 can be sized slightly smaller than the gel reservoir top portions 422. This size difference allows the smaller gel reservoir inner portions 432 to nest within the gel reservoir top portions 422 and define the air gap there-between. With such an arrangement of components, upon application of an exerted pressure from a pressurized fluid, pressure within the air gap can increase until an adhesive seal ruptures. When the adhesive seal ruptures, the exerted pressure can deform the gel reservoir inner portion 432, thereby causing flow of the conductive gel contained within that conductive gel reservoir 404.

The multilayer assembly as shown in FIG. 4B can further include a lidding layer 440. The lidding layer 440 is configured to adhere to the diaphragm layer 430 to provide a sealing surface for holding the conductive gel within gel reservoir inner portions 432 of the diaphragm layer 430. The lidding layer 440 can be formed from, for example, a polyester film that includes a heat sealable adhesive layer. In some examples, Scotchpak™ MA250M Medical Adhesion Film can be used for the construction of the lidding layer 440. Similar to the ionomer resin sheet as described above, the thickness of the polyester film can be selected based upon the desired flexibility of the finished lidding layer 440. In some examples, the thickness of the ionomer resin sheet can be between 0.00230-0.00260 inches thick. In certain implementations, the thickness of the ionomer resin sheet can be 0.00245 inches thick. Additionally, like the ionomer resin as described above, a polyester film with a low permeability and water vapor transmission rate can be selected. Additional characteristics such as adhesive density and other related properties can also be determined based upon resulting desired characteristics of the finished lidding layer 440.

As described above, the lidding layer 440 can be configured to act as barrier layer preventing unwanted release of the conductive gel from the conductive gel reservoirs 404. As such, the adhesive seals 410 can be placed between the diaphragm layer 430 and the lidding layer 440. Similarly, the lidding layer 440 includes exit ports 412 (as shown in FIG. 4A) positioned adjacent to (or, if a ring-shaped adhesive seal is used, in the center of) the adhesive seals 410.

When manufactured, the outer layer 420, the diaphragm layer 430 and the lidding layer 440 can be combined into a multilayer gel deployment device 401. As noted above, the gel deployment device 401 can be configured to deploy an amount of conductive gel prior to application of, for example, a therapeutic shock.

As noted above, a therapy electrode 400 can also include an electrically conductive layer 450. The electrically conductive layer 450 can be formed from a conductive material such as metal foil or another thin, pliable conductive material. For example, the electrically conductive layer 450 can be constructed from rolled stainless steel. In some examples, the thickness of the electrically conductive layer 450 can be between 0.00295-0.00305 inches thick. In certain implementations, the thickness of the electrically conductive layer 450 can be 0.003 inches thick.

The electrically conductive layer 450 can be configured to be positioned substantially proximate to the patient's skin and to direct a therapeutic shock towards the patient's skin. Depending upon the design, the electrically conductive layer 450 can also be integrated directly into the garment, e.g., garment 110 as described above. In certain implementations, the electrically conductive layer 450 is positioned and configured to work in concert with the gel deployment device 401. This provides for a replaceable gel deployment device 401 that can be replaced without replacing the electrically conductive layer 450 as well.

Additionally, the electrically conductive layer 450 can include a series of apertures 452. The apertures 452 can be arranged in a similar geometry as the placement of the adhesive seals 410 and the exit ports 412 (as shown, for example, in FIG. 4A). Such an arrangement of components provides for conductive gel flow through the exit ports 412 and then through the apertures 452 in the electrically conductive layer 450 and onto a patient's skin.

As noted above, each of the lidding layer 440 and the electrically conductive layer 450 includes one or more exit ports in the lidding layer 440 (e.g., exit ports 412 as shown in FIG. 4A) and apertures 452 in the electrically conductive layer 450 positioned such that the exit ports 412 and apertures 452 are aligned with the open center portion of gel reservoir cluster 403. Depending upon the manufacturing process, the exit ports 412 and apertures 452 can be formed in the lidding layer 440 and the electrically conductive layer 450 prior to or during assembly of the multilayer device illustrated in FIG. 4B. For example, the open center portion of the gel reservoir clusters 403 can be used to align a piercing device configured to pierce the multilayered device to produce the exit ports 412 and the apertures 452. However, if such a process is used, for example, to stamp out the exit ports 412 and the apertures 452 after assembly of the multilayered assembly, a sealant or adhesive plug (not shown in FIG. 4B) can be applied to the outer layer 420 to prevent unwanted fluid flow upon release of the conductive gel.

In an example manufacturing process, each layer as shown in FIG. 4B can configured to be adhered to its adjacent layers via an adhesion process. For example, each of the outer layer 420 and the diaphragm layer 430 can be bonded together directly. Heat and pressure can be applied to each of the outer layer 420 and the diaphragm layer 430 to, e.g., chemically bond the two layers together. As noted above, the lidding layer 440 can be manufactured from a polyester film that includes a heat-activated adhesive. In such an arrangement of components, the diaphragm layer 430 (or the combined top layer 420 and diaphragm layer 430) can be positioned on top of the lidding layer 440 such that the lidding layer 440 acts to seal the conductive gel in the gel reservoir inner portions 432 of the diaphragm layer 430. Heat can be applied to the stacked structure, thereby forming the multilayer gel deployment device as described above. Additionally, an amount of heat-activated adhesive (or another similar adhesive) can be applied between the lidding layer 440 and the electrically conductive layer 450. The electrically conductive layer 450 can then be adhered to the lidding layer 440 (and, subsequently, the multilayered gel deployment device), thereby resulting in a complete therapy electrode 400.

In certain implementations, the therapy electrode 400 can be configured to include one or more ventilation holes (e.g., similar to ventilation holes 226, 234 and 242 as shown in FIG. 2C) or one or more openings (e.g., similar to opening 254 shown in FIG. 2C) in the electrically conductive layer 450 to increase edge length. FIGS. 4A and 4B are provided by way of example only and can be altered to include additional features such as the ventilation holes and openings in the electrically conductive layer as described above.

In operation, the therapy electrode 400 as describe above can be configured to provide a therapeutic shock to a patient current experiencing, for example, a cardiac arrhythmia. Prior to delivering the shock, the conductive gel deployment device 401 associated with the therapy electrode 400 can be configured to deploy the conductive gel onto the patient's skin. Initially, the pressure source 406 can be triggered to produce an increased fluid pressure in the fluid channel 408. The increased fluid pressure can cause internal pressure within the air gaps between each gel reservoir top portion 422 and its corresponding gel reservoir inner portion 432 to increase. As the internal pressure within the conductive gel reservoirs 404 increases, a distributed pressure can be applied about the perimeter of each of the adhesive seals 410 for each of the reservoir clusters 403. After the distributed pressure reaches a high enough level (e.g., 8-22 psi), each individual adhesive seal 410 can begin to rupture, causing the release of the conductive gel from each of the conductive gel reservoirs 404. Pressure within each of the conductive gel reservoirs 404 can cause deformation of the gel reservoir inner portion 432, which results in the conductive gel being pushed out of the conductive gel reservoirs 404. The conductive gel can flow through the exit ports 412 for each reservoir cluster 403 and can be distributed on the electrically conductive surface 450 and the patient's skin. After gel deployment, the electrically conductive surface 450 can direct the therapeutic shock through the conductive gel, which conducts the therapeutic shock to the patient's skin.

Figure 5:
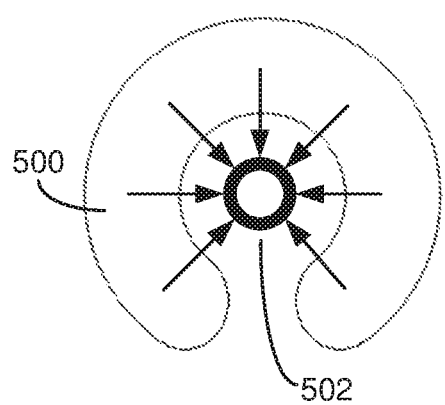
FIG. 5 depicts an example of a conductive gel reservoir, in accordance with an example of the present disclosure.

As described above in the description of FIGS. 2A-2C, and 4A and 4B, a conductive gel reservoir (or a cluster of conductive gel reservoirs) can be arranged such that it surrounds a single adhesive seal. With such an arrangement of components, a pressure exerted on the adhesive seal is substantially equally distributed about the perimeter of the adhesive seal. However, additional conductive gel reservoir designs can be used that also improve distribution of an exerted pressure as compared to conventional designs. For example, as shown in FIG. 5, a conductive gel reservoir 500 can have a U or horseshoe shape such that the conductive gel reservoir 500 partially surrounds its adjacent adhesive seal 502. For example, the conductive gel reservoir 500 can be configured to surround approximately 180°-345° of the adhesive seal 502. In certain implementations, the conductive gel reservoir 500 can be configured to surround approximately 315° of adhesive seal 502. However, when a pressure is exerted on the conductive gel reservoir 500, the conductive gel reservoir exerts a similar pressure about the perimeter of the adhesive seal 502. As indicated by the various arrows shown in FIG. 5, the exerted pressure can be applied to the adhesive seal 502 at multiple points about the perimeter of the adhesive seal 502.

The configuration as shown in FIG. 5 can offer an advantage over a configuration involving an adhesive seal configured to rupture from pressure being applied at only a single point. For instance, multiple points of applied pressure to the adhesive seal 502 can improve a likelihood that the adhesive seal 502 will be subjected to pressures at or about the predetermined pressure level configured to rupture the adhesive seal 502, thereby increasing the likelihood that each of the multiple points of the adhesive seal 502 will rupture, providing more area for the conductive gel to flow out of the conductive gel reservoir 500.

It should be noted that the size and shape of conductive gel reservoir 500 as shown in FIG. 5 is by way of example, and various other sizes and shapes can be included. For example, the conductive gel reservoir 500 can have a semi-circular shape configured to surround about 180° of the perimeter of the adhesive seal 502. In certain implementations, the conductive gel reservoir 500 can have a C-shape configured to surround about 210°-270° of the perimeter of the adhesive seal 502.

In some implementations, a gel deployment device can include fluid conduits fluidly connected to one or more conductive gel reservoirs. In such an implementation, when a pressurized fluid is applied to the conductive gel reservoir, the pressure exerted by the pressurized fluid is distributed about a perimeter of an adhesive seal positioned between the conductive gel reservoir and a fluid conduit. Once the pressure reaches a predetermined pressure level configured to rupture the adhesive seal (e.g., in the range of 8-22 psi), the adhesive seal ruptures, thereby resulting in release of the conductive gel stored in the conductive gel reservoir. After release, the conductive gel can flow through the fluid conduits to multiple exit ports along the path of the fluid conduit. With such an arrangement of components, multiple exit ports can be in fluid connection with a single adhesive seal, thereby reducing the number of adhesive seals used in the gel deployment device. Additionally, such an arrangement of components has the advantage of reducing or eliminating leaking due to improperly ruptured adhesive seals. In certain embodiments, if an adhesive seal were to prematurely rupture, the released conductive gel would can flow into the fluid conduits and remain there until an applied pressure pushes the conductive gel through the fluid conduits to the exit ports.

Figure 6A:
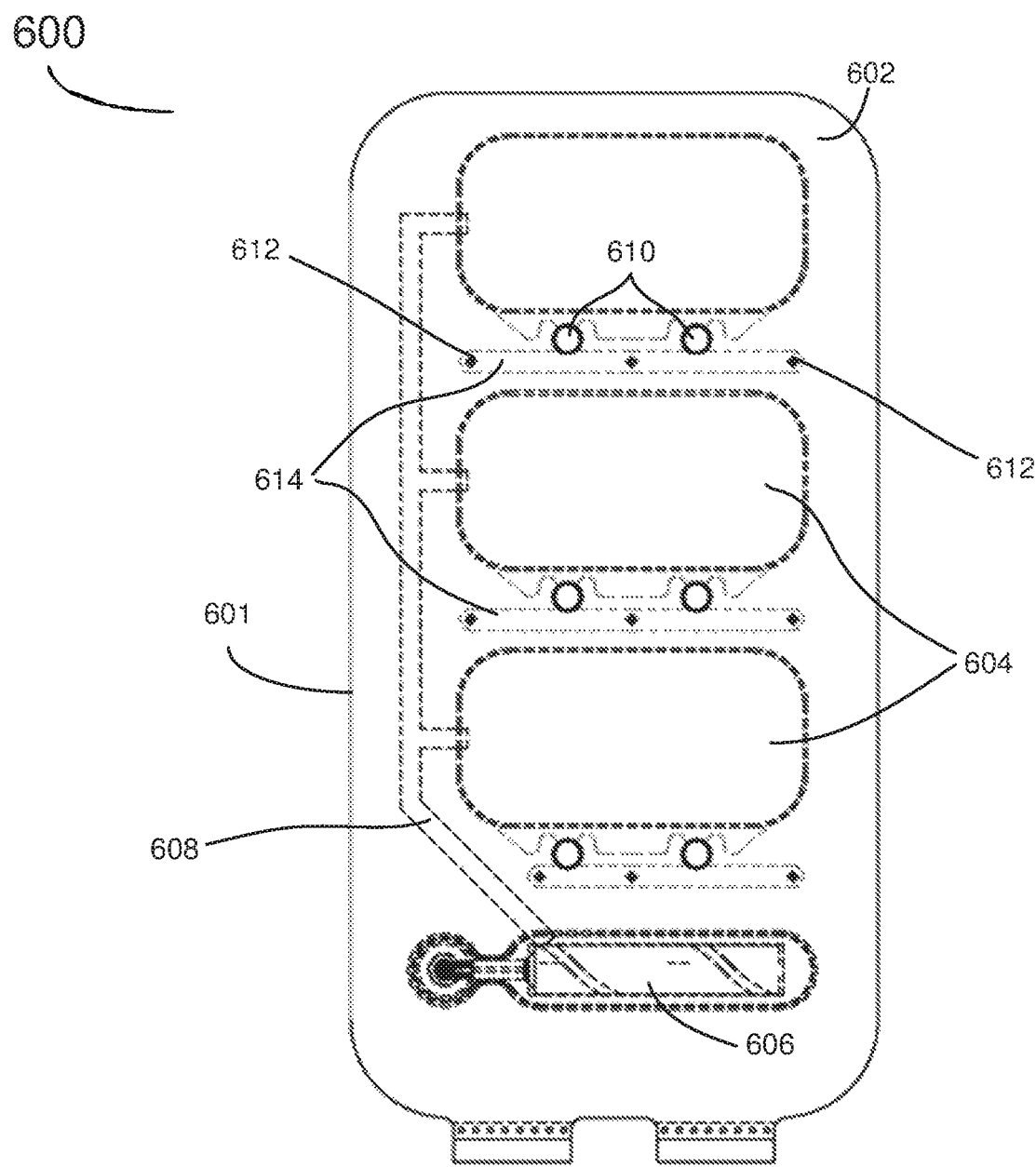
FIG. 6A depicts a plan view of a therapy electrode, in accordance with an example of the present disclosure.
Figure 6B:
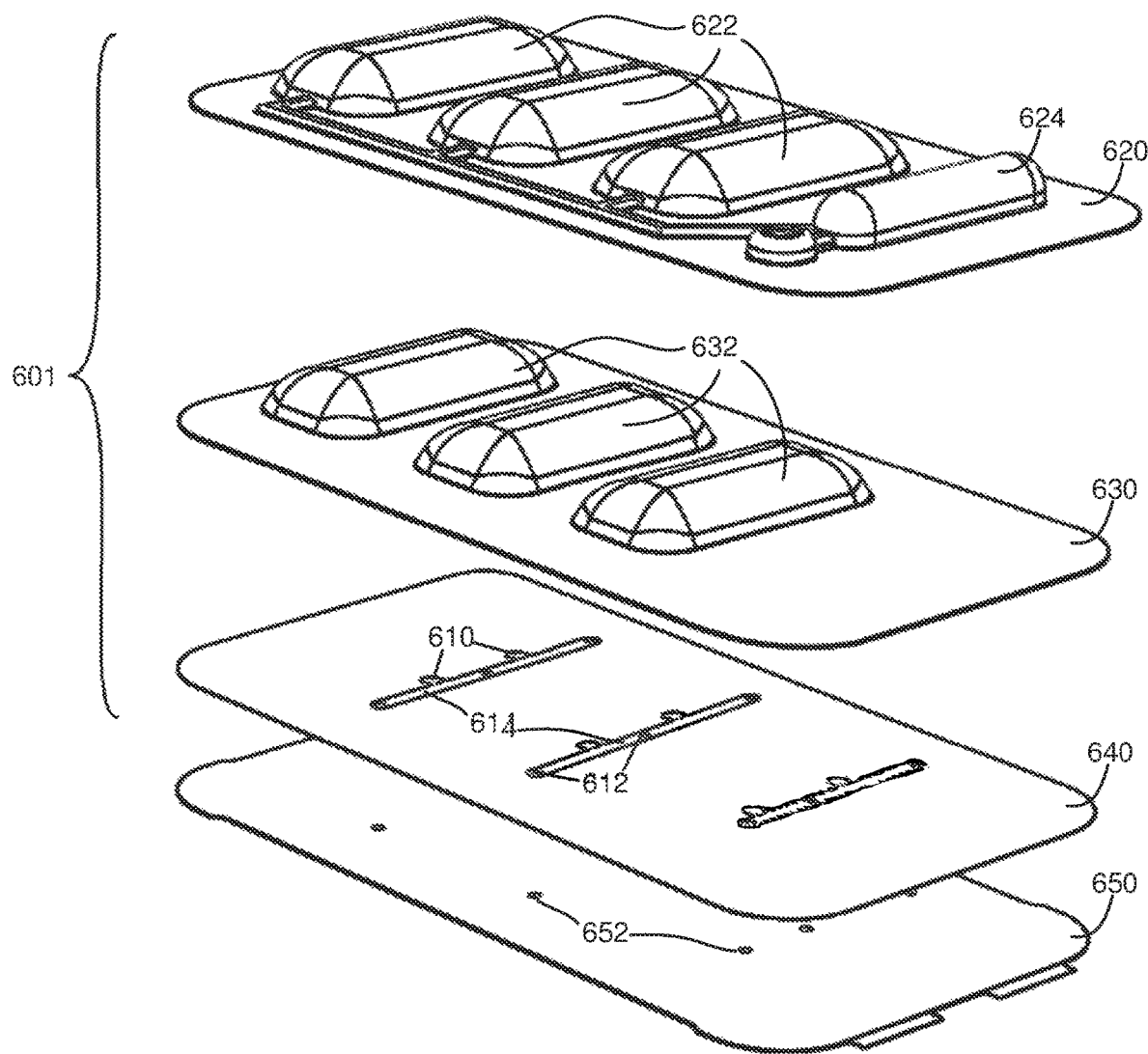
FIG. 6B depicts an exploded view of the therapy electrode of FIG. 5A.

FIGS. 6A and 6B illustrates a therapy electrode 600 including a conductive gel deployment device 601 that uses conductive gel reservoirs having gel conduits for directing conductive gel flow. This configuration can include, for example, redundant adhesive seals for each conductive gel reservoir (e.g., two or more adhesive seals for each gel conduit). Upon application of pressure to the conductive gel reservoirs (e.g., from a pressure source as described in further detail below), the conductive gel in turn exerts a pressure on the adhesive seals until one or more of the adhesive seals rupture. The pressure then aids in the flow of the conductive gel through one or more conductive gel conduits to one or a series of distributed exit ports. For example, the exit ports can be spaced apart on the substrate to allow for even distribution of the conductive gel on a conductive surface in proximity to the patient's skin.

FIG. 6A illustrates a therapy electrode 600 that includes a conductive gel deployment device 5601 using, for example in this configuration, multiple gel conduits 614 for distribution of conductive gel. Like therapy electrode 200, the therapy electrode 600 can be a multiple layer laminated structure that includes an electrically conductive layer 650 (shown in FIG. 6B and explained in greater detail below). In use, the electrically conductive layer 650 can be disposed substantially proximate to the patient's skin, although the conductive layer need not make direct contact with the patient (e.g., in implementations where conductive portions of the garment 110 act as an interface between the conductive layer 650 and the patient's skin, and/or implementations where portions of the patient's clothing may be present between the electrically conductive layer 650 and the patient's skin). In some implementations, the garment 110 can include a pocket or other similar structure including a metallic mesh that can be configured to act as an interface between the electrically conductive layer 650 and the patient's skin. Upon deployment of the conductive gel, an electrical pathway can be defined between the electrically conductive layer 650 and the patient's skin.

As shown in FIG. 6A, the therapy electrode 600 can include a substrate 602 about which various components of the gel deployment device 601 can be arranged. The substrate 602 can include a plurality of conductive gel reservoirs 604 distributed about the surface of the substrate 602. In certain implementations, the conductive gel reservoirs 604 can be disposed about a first side of the substrate 602 (e.g., a top portion of the substrate 602 as depicted in the plan view of FIG. 6A and positioned opposite a bottom portion or side of the therapy electrode 600 that includes, for example, the conductive layer 650). Each of the conductive gel reservoirs 604 can be configured to hold a volume of conductive gel. Depending upon the total number of conductive gel reservoirs 604 used, the amount of conductive gel contained within each conductive gel reservoir 604 can be adjusted accordingly. For example, the gel deployment device 601 can include approximately 3-20 ml of conductive gel. In other examples, the gel deployment device 601 can be configured to hold between 5-15 ml of conductive gel. The conductive gel can be distributed amongst each of the conductive gel reservoirs 604. For example, each conductive gel reservoir 604 can be configured to hold approximately 0.5-5.0 ml of conductive gel. In other examples, each conductive gel reservoir 604 can be configured to hold between 1.0 and 4.0 ml of conductive gel. In come implementations, depending upon the number and shape of the conductive gel reservoirs 604, additional quantities of conductive gel can be included in each conductive gel reservoir 604. For example, each conductive gel reservoir 604 can be configured to hold 6 ml of conductive gel, 7 ml of conductive gel, 8 ml of conductive gel, 9 ml of conductive gel, or 10 ml of conductive gel. As such, by varying the amount of total conductive gel held within each conductive gel reservoir 604, the total amount of gel contained within gel deployment device 601 can be adjusted.

In certain embodiments, the amount of conductive gel in each of the conductive gel reservoirs 604 can be equal or substantially equal such that the total amount of conductive gel is distributed among each of the conductive gel reservoirs 604. In other examples, the amount of conductive gel in each of the conductive gel reservoirs 604 can vary.

As shown in the example gel deployment device 601 illustrated in FIG. 6A, with three conductive gel reservoirs 604, each conductive gel reservoir 604 can hold approximately 3.34 ml of conductive gel. As noted above, in other examples, a gel deployment device can be configured to hold between approximately 3 ml and 20 ml of conductive gel. The amount of conductive gel can be determined based upon the number of reservoirs being used as well as the size of the electrically conductive layer the conductive gel is configured to be deployed on.

Additionally, the therapy electrode 600 can also include a set of conductive gel reservoir protective caps like protective caps 205 and 405 as described above. The protective caps can be configured to cover the conductive gel reservoirs 604 to provide protection. In certain implementations, the protective caps can be made from a hard plastic such as polystyrene or polycarbonate. The protective caps can be sized (e.g., have a preconfigured thickness) such that the protective caps provide a rigid outer structure for absorbing any accidental force or pressure exerted on the outside of the conductive gel reservoirs 604 prior to release of the conductive gel contained therein. In certain configurations, each of the conductive gel reservoirs 604 can have a single protective cap. In other implementations, the protective caps can be sized to protect multiple conductive gel reservoirs 604.

Each of the conductive gel reservoirs 604 can also include one or more adjacent adhesive seals 610, such as ring-shaped adhesive seals. As shown in FIG. 6A, each conductive gel reservoir can include two adhesive seals 610, thereby providing for a redundant release mechanism for the conductive gel contained within each conductive gel reservoir 604. The adhesive seals 610 are positioned such that they can prevent release of the conductive gel to the exit ports 612 (via the gel conduits 614).

The therapy electrode 600 can further include a pressure source 606 connected to a fluid channel 608. The pressure source 606, when activated by an activation signal, can release a fluid, such as compressed gas, into the fluid channel 608. The hydraulic pressure of the fluid from the activated fluid pressure source 606 in the fluid channel 608 facilitates release of the adhesive seals 610 at or about substantially at a predetermined pressure level configured to rupture the adhesive seal 610. In an example, as a result of the position of the adhesive seals 610 relative to their adjacent conductive gel reservoir 604, the pressure exerted by the pressure source 606 can cause the conductive gel to, in turn, exert a pressure against the adhesive seals 610. Thus, the adhesive seals 610 can be configured to rupture at one or more points where the conductive gel exerts the pressure on the adhesive seal 610 (or in a continuous portion of the adhesive seal 610 in contact with the conductive gel), at or about substantially at the predetermined pressure level configured to rupture the adhesive seal 610, thereby resulting in release of the conductive gel from each conductive gel reservoir 604.

As shown in FIG. 6A, adhesive seals 610 can be ring-shaped adhesive seals. In such an arrangement, the adhesive seal 610 can include multiple barriers to prevent conductive gel flow. For example, as shown in FIG. 6A, the portion of the adhesive seal 610 that is positioned substantially proximate to the conductive gel reservoir 604 (i.e., the top portion of the seal 610 as shown in FIG. 6A) can provide a first barrier configured to prevent release of the conductive gel from the conductive gel reservoir 604. Similarly, the portion of the adhesive seal 610 that is positioned substantially proximate to the gel conduit 614 (i.e., the bottom portion of the ring-shaped adhesive seal 610 as shown in FIG. 6A) can provide a second barrier. In the event of a premature failure of the top portion of the adhesive seal 610, the bottom portion of the adhesive seal 610 can provide a redundant seal, thereby lowering the chances of a leaking conductive gel reservoir as compared to designs with a single adhesive seal barrier. Thus, in such an example, once the pressure exerted by the conductive gel has ruptured the top portion of the adhesive seal 610, the conductive gel can flow through the adhesive seal 610 until the conductive gel contacts the bottom portion of the adhesive seal 610. As before, the conductive gel can apply a pressure to the bottom portion of the adhesive seal 610, thereby causing the bottom portion to rupture. The conductive can then flow into one of the gel conduits 614.

It should be noted that ring-shaped adhesive seals are shown in FIG. 6A and described above by way of example only. In certain implementations, the adhesive seal can be shaped as a straight or curved line that is configured to define a single barrier to prevent conductive gel flow. Such an implementation can be advantageous when the design includes a fluid pressure source configured to release a pressurized fluid having a lower pressure, e.g., 4-15 psi. In such an example, as a result of the lower pressure of the pressurized fluid, it can be advantageous to have a single barrier that is configured to be ruptured prior to conductive gel release.

Upon release of the adhesive seals 610, the conductive gel stored in each of the plurality of conductive gel reservoirs 604 can flow into one of the gel conduits 614. The released conductive gel can continue to flow through the gel conduits 614 to the plurality of exit ports 612. The conductive gel can then flow through apertures formed in the electrically conductive layer 650 and onto the exposed surface of the electrically conductive layer 650 proximate to the patient's skin. The apertures in the electrically conductive layer 650 are substantially aligned with the plurality of exit ports 612 so that, when released, the electrically conductive gel is dispensed onto the exposed surface of the electrode portion that is disposed substantially proximate to the patient's body.

It should be noted that the arrangement and position of both the gel conduits 614 and the exit ports 612 as shown in FIG. 6A is by way of example only. For example, the path of conductive gel flow as defined by the gel conduits 614 can include a curved or other non-linear shape in addition to the linear shape shown in FIG. 6A. Similarly, more or less than the three exit ports 612 per gel conduit 614 as shown in FIG. 6A can be included. Thus, by altering the shape of the gel conduits 614 and the number of exit ports 612, the conductive gel can be more evenly distributed about the therapy electrode 600 without increasing the number of conductive gel reservoirs 604 and adhesive seals 610.

FIG. 6B illustrates an exploded view of the therapy electrode 600, showing the multiple layers included in the manufacturing process of the therapy electrode 600. In certain implementations, a set of layers as shown in FIG. 6B (e.g., layer 620, 630 and 640 as described in greater detail below) can be assembled to manufacture the gel deployment device 601. It should be noted that the details provided in FIG. 6B and explained herein, as well as the overall process discussed below, is provided by way of example only. For example, changes to the techniques and configurations described herein can be implemented without substantially deviating from the scope of the disclosure.

The multilayer assembly as shown in FIG. 6B can include an outer layer 620. The outer layer 620 can be formed from, for example, various polymers such as formed thermoplastic. In some implementations, the outer layer 620 can be constructed from an ethylene acid copolymer. In some examples, a copolymer having a low water vapor transmission rate can be chosen. For example, the outer layer 620 can be constructed from an ionomer resin of ethylene acid copolymer such as DuPont™ Surlyn® as described above. Such a resin can be processed in conventional blown film, cast film, sheet extrusion and coextrusion equipment designed to process polyethylene and ethylene copolymer type resins. The ionomer resin can be configured to have a relatively low water vapor transmission rate (e.g., 0.8 g/100 in$^2$/day). For example, a material with a low permeability such as an ionomer resin can provide an advantage of a longer shelf-life of the conductive gel deployment device relative to conventional configurations as the rate of evaporation of the conductive gel through the ionomer resin is low. Thus, the conductive gel inside the conductive gel reservoirs (e.g., conductive gel reservoirs 604) can maintain its original viscosity when stored in the conductive gel reservoirs for an extended period of time (e.g., for a period of two or more years).

In some examples, the outer layer 620 can be manufactured from the ionomer resin using a vacuum forming machine. A vacuum forming process can be used to form a sheet of the ionomer resin into the outer layer 620. An appropriately sized sheet of the ionomer resin can be placed into the vacuum forming machine along with a mold or plate including a negative of the features to be formed on the outer layer 620. The sheet of the ionomer resin can be appropriately heated, stretched against the mold, and pressed against the mold by a vacuum pressure. After the pressure is released, the sheet of ionomer resin has been molded into the outer layer 620. Based upon the resulting desired characteristics of the outer layer 620, the physical properties of the ionomer resin sheet can be chosen or adjusted accordingly. For example, the thickness of the ionomer resin sheet can be selected based upon the desired flexibility of the finished outer layer 620 as well as the pressures that will be exerted on the outer layer 620. In some examples, the thickness of the ionomer resin sheet can be between 0.0095-0.0120 inches thick. In certain implementations, the thickness of the ionomer resin sheet can be 0.011 inches thick. Additional characteristics such as resin density and other related properties can also be determined based upon resulting desired characteristics of the finished outer layer 620.

The outer layer 620 can include multiple gel reservoir top portions 622. The gel reservoir top portions 622 can be formed to provide an air pocket as well as a surface against which a pressurized fluid can exert a pressure when applied to a conductive gel reservoir 604. Similarly, the outer layer 620 can include a pressure source top portion 624. The pressure source top portion 624 can be arranged to define a cavity for insertion and containment of, for example, pressure source 606.

The multilayer assembly as shown in FIG. 6B can also include a diaphragm layer 630. Like the outer layer 620, the diaphragm layer 630 can be formed from, for example, an ionomer resin. As before, a vacuum forming process can be used to form a sheet of the ionomer resin into the diaphragm layer 630. An appropriately sized sheet of the ionomer resin can be placed into the vacuum forming machine along with a mold or plate including a negative of the features to be formed on the diaphragm layer 630. The sheet of the ionomer resin can be appropriately heated, stretched against the mold, and pressed against the mold by a vacuum pressure. After the pressure is released, the sheet of ionomer resin has been molded into the diaphragm layer 630. Based upon the resulting desired characteristics of the diaphragm layer 630, the physical properties of the ionomer resin sheet can be chosen or adjusted accordingly. For example, the thickness of the ionomer resin sheet can be selected based upon the desired flexibility of the finished diaphragm layer 630. In some examples, the thickness of the ionomer resin sheet can be between 0.0095-0.0120 inches thick. In certain implementations, the thickness of the ionomer resin sheet can be 0.011 inches thick. Additional characteristics such as resin density and other related properties can also be determined based upon resulting desired characteristics of the finished diaphragm layer 630.

The diaphragm layer 630 can also include multiple gel reservoir inner portions 632. The gel reservoir inner portions 632 can be formed such that, upon layering of the outer layer 620 and the diaphragm layer 630, a small air gap is defined between each gel reservoir top portion 622 and a corresponding gel reservoir inner portion 632. As such, the gel reservoir inner portions 632 can be sized slightly smaller than the gel reservoir top portions 622. This size difference allows the smaller gel reservoir inner portions 632 to nest within the gel reservoir top portions 622 and define the air gap there-between. With such an arrangement of components, upon application of an exerted pressure from a pressurized fluid, pressure within the air gap can increase until an adjacent adhesive seal ruptures. When the adhesive seal ruptures, the exerted pressure can deform the gel reservoir inner portion 632, thereby causing flow of the conductive gel contained within that conductive gel reservoir 604.

The multilayer assembly as shown in FIG. 6B can further include a lidding layer 640. The lidding layer 640 is configured to adhere to the diaphragm layer 630 to provide a sealing surface for holding the conductive gel within gel reservoir inner portions 632 of the diaphragm layer 630. The lidding layer 640 can be formed from, for example, a polyester film that includes a heat sealable adhesive layer. In some examples, Scotchpak™ MA250M Medical Adhesion Film can be used for the construction of the lidding layer 640. Similar to the ionomer resin sheet as described above, the thickness of the polyester film can be selected based upon the desired flexibility of the finished lidding layer 640. In some examples, the thickness of the ionomer resin sheet can be between 0.00230-0.00260 inches thick. In certain implementations, the thickness of the ionomer resin sheet can be 0.00245 inches thick. Additionally, like the ionomer resin as described above, a polyester film with a low permeability and water vapor transmission rate can be selected. Additional characteristics such as adhesive density and other related properties can also be determined based upon resulting desired characteristics of the finished lidding layer 640.

As described above, the lidding layer 640 can be configured to act as barrier layer preventing unwanted release of the conductive gel from the conductive gel reservoirs 604. As such, the adhesive seals 610 can be placed between the diaphragm layer 630 and the lidding layer 640. Similarly, the lidding layer 640 includes exit ports 612 positioned adjacent to the adhesive seals 610. Additionally, the lidding layer 640 can include one or more pathway features used to define the fluid conduits 614. For example, one or more pieces of porous material such as foam can be positioned appropriately on the lidding layer 640 such that, when placed against the diaphragm layer 630, the foam pieces act to define the fluid conduits 614.

When manufactured, the outer layer 620, the diaphragm layer 630 and the lidding layer 640 can be combined into the multilayer gel deployment device 601. As noted above, the gel deployment device 601 can be configured to deploy an amount of conductive gel prior to application of, for example, a therapeutic shock.

As noted above, a therapy electrode 600 can also include an electrically conductive layer 650. The electrically conductive layer 650 can be formed from a conductive material such as metal foil or another thin, pliable conductive material. For example, the electrically conductive layer 650 can be constructed from rolled stainless steel. In some examples, the thickness of the electrically conductive layer 650 can be between 0.00295-0.00305 inches thick. In certain implementations, the thickness of the electrically conductive layer 650 can be 0.003 inches thick.

The electrically conductive layer 650 can be configured to be positioned substantially proximate to the patient's skin and to direct a therapeutic shock towards the patient's skin. Depending upon the design, the electrically conductive layer 650 can also be integrated directly into the garment, e.g., garment 110 as described above. In certain implementations, the electrically conductive layer 650 is positioned and configured to work in concert with the gel deployment device 601. This provides for a replaceable gel deployment device 601 that can be replaced without replacing the electrically conductive layer 650 as well.

Additionally, the electrically conductive layer 650 can include a series of apertures 652. The apertures 652 can be arranged in a similar geometry as the placement of the adhesive seals 610 and the exit ports 612. Such an arrangement of components provides for conductive gel flow through the exit ports 612 and then through the apertures 652 in the electrically conductive layer 650 and onto a patient's skin.

In an example manufacturing process, each layer as shown in FIG. 6B can be configured to be adhered to its adjacent layers via an adhesion process. For example, each of the outer layer 620 and the diaphragm layer 630 can be bonded together directly. Heat and pressure can be applied to each of the outer layer 620 and the diaphragm layer 630 to, e.g., chemically bond the two layers together. As noted above, the lidding layer 640 can be manufactured from a polyester film that includes a heat-activated adhesive. In certain implementations, the diaphragm layer 630 (or the combined top layer 620 and diaphragm layer 630) can be positioned on top of the lidding layer 640 such that the lidding layer 640 acts to seal the conductive gel in the gel reservoir inner portions 632 of the diaphragm layer 630. Heat can be applied to the stacked structure, thereby forming the multilayer gel deployment device as described above. Additionally, an amount of heat-activated adhesive (or another similar adhesive) can be applied between the lidding layer 640 and the electrically conductive layer 650. The electrically conductive layer 650 can then be adhered to the lidding layer 640 (and, subsequently, the multilayered gel deployment device), thereby resulting in a complete therapy electrode 600.

In certain implementations, the therapy electrode 600 can be configured to include one or more ventilation holes (e.g., similar to ventilation holes 226, 234 and 242 as shown in FIG. 2C) or more or more openings (e.g., similar to opening 254 as shown in FIG. 2C) in the electrically conductive layer to increase edge length. FIGS. 6A and 6B are provided by way of example only to and can be altered to include additional features such as the ventilation holes and openings in the electrically conductive layer as described above.

In operation, the therapy electrode 600 as describe above can be configured to provide a therapeutic shock to a patient current experiencing, for example, a cardiac arrhythmia. Prior to delivering the shock, the conductive gel deployment device 601 associated with the therapy electrode 5600 can be configured to deploy the conductive gel onto the patient's skin. Initially, the pressure source 606 can be triggered to produce an increased fluid pressure in the fluid channel 608. The increased fluid pressure can cause internal pressure within the air gaps between each gel reservoir top portion 622 and its corresponding gel reservoir inner portion 632 to increase. As the internal pressure within the conductive gel reservoirs 604 increases, a distributed pressure can be applied to each of the adhesive seals 610. After the distributed pressure reaches a high enough level (e.g., 8-22 psi), each individual adhesive seal 610 can begin to rupture, causing the release of the conductive gel from each of the conductive gel reservoirs 604. Pressure within each of the conductive gel reservoirs 604 can cause deformation of the gel reservoir inner portion 632, which results in the conductive gel being pushed out of the conductive gel reservoirs 604. The distributed pressure can facilitate gel flow into the gel conduits 614 and through each of the exit ports 612. The conductive gel can flow through the exit ports 612 and can be distributed on the electrically conductive surface 650 and the patient's skin. After conductive gel deployment, the electrically conductive surface 650 can direct the therapeutic shock through the conductive gel, which conducts the therapeutic shock to the patient's skin.

Use of a Gel Deployment Device with an Ambulatory Medical Device

Figure 7:
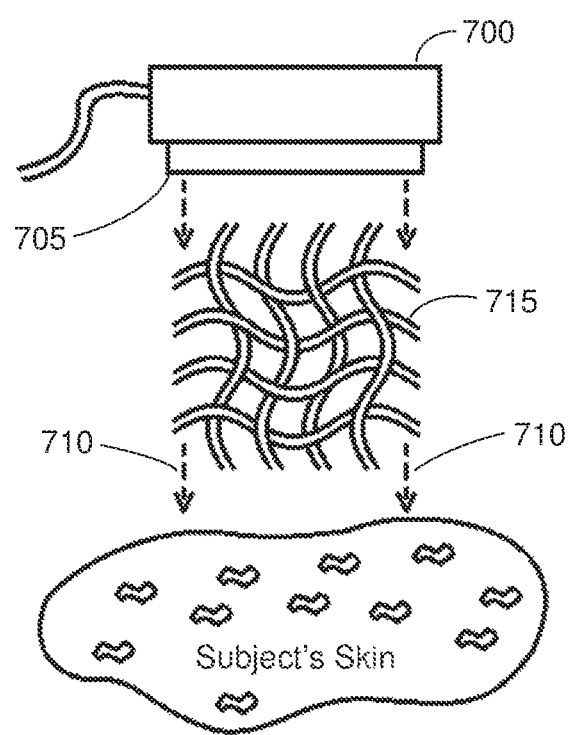
FIG. 7 depicts an interface between a therapy electrode and a patient's skin in accordance with an example of the present disclosure.

FIG. 7 depicts an example of conductive gel entering the area between a therapy electrode and the patient's skin after being released by, for example, one of the gel deployment devices as described above (e.g., gel deployment devices 201, 401 and 601 as shown in FIGS. 2C, 4B and 6B). In one implementation, the conductive gel can enter the area between a conductive surface 705 of therapy electrode 700 and the patient's skin, and can form a conduction path 710 from the therapy electrode 700 to the patient's skin. The conductive gel can cover conductive thread or mesh fabric 715 that is part of a garment (e.g., garment 110), portions of which can be disposed between the patient's skin and the therapy electrode 700. For example, the gel deployment device can be configured in a form of a removable receptacle. As such, after the gel is deployed, the gel deployment device can be removed and replaced.

Figure 8:
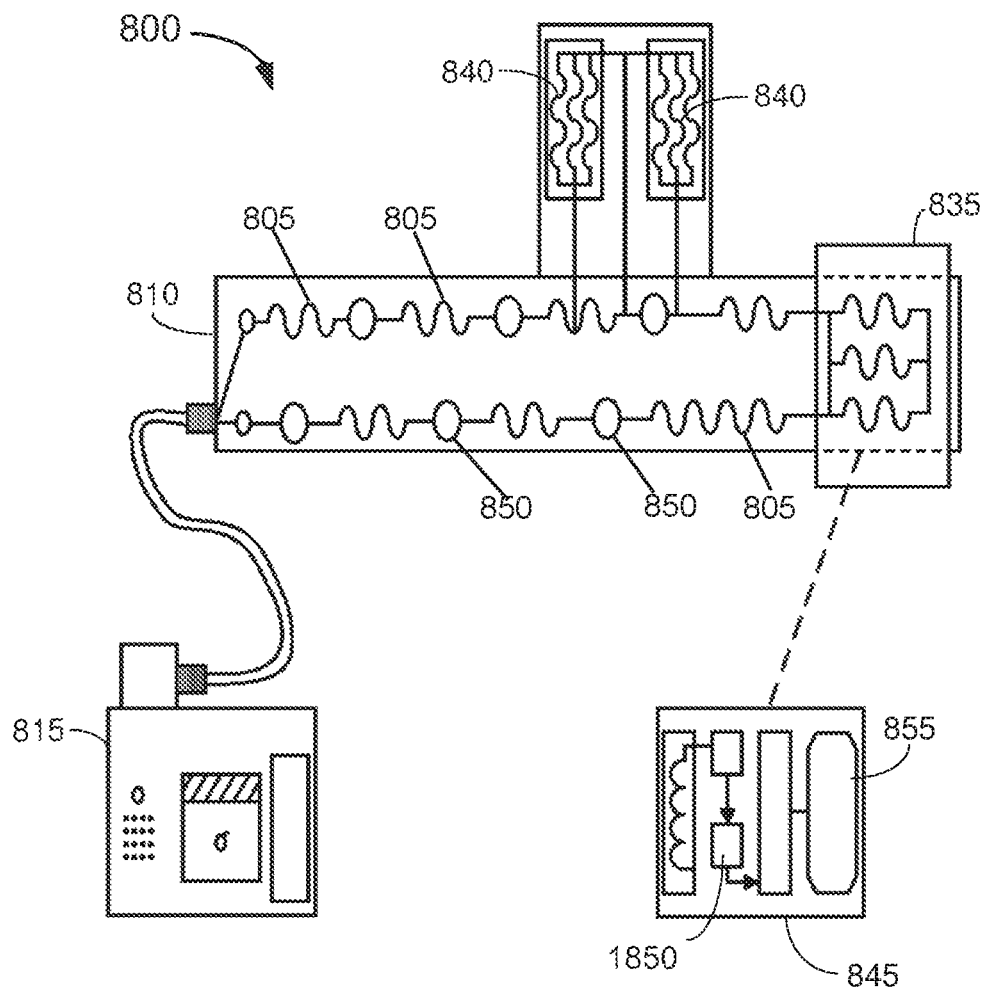
FIG. 8 depicts a schematic diagram illustrating various components of an external medical device in accordance with an example of the present disclosure.

FIG. 8 illustrates components of external medical device 800 according to certain implementations, with sensing electrodes 850 including at least one EKG (or ECG) electrocardiogram sensor, conductive thread 805 woven into belt 810 of garment 110, and gel deployment device 845 disposed proximate to a first therapy electrode 835 in garment 810.

In one implementation, a control unit 850 can instruct the gel deployment device 845 to release the conductive gel included in conductive gel reservoir 855. The released conductive gel can reduce impedance between the patient's skin and first therapy electrode 835. Therapy controller 815 can apply treatment (e.g., a shock) to the patient via first therapy electrode 835 and second therapy electrode 840 (that can include another gel deployment device 845 for deployment of conductive gel between second therapy electrode 840 and the patient's skin). During treatment, current can follow a path between the patient's skin and first therapy electrode 835 and second therapy electrode 840 via the conductive gel.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A wearable defibrillator electrotherapy delivery device to promote comfort of an ambulatory patient, the device comprising:
   a conductive surface configured to be in electrical contact with skin of the ambulatory patient and provide a therapeutic shock to the patient;
   a multilayer substrate, wherein each layer of the multilayer substrate includes one or more ventilation holes; and
   one or more ventilation holes disposed on the conductive surface, wherein the one or more ventilation holes of each layer of the multilayer substrate are aligned with the one or more ventilation holes disposed on the conductive surface to provide air flow to the skin of the patient when the device is worn, and wherein the one or more ventilation holes disposed on the conductive surface are larger than any of the one or more ventilation holes of each layer of the multilayer substrate.

2. The device of claim 1, further comprising:
   one or more gel reservoirs disposed on the multilayer substrate and comprising a quantity of gel to be released to the skin of the patient prior to treatment of the patient.

3. The device of claim 2, further comprising:
   a fluid pressure source in fluid communication with the one or more gel reservoirs; and
   at least one rupturable seal in fluid communication with the one or more gel reservoirs, the at least one rupturable seal being configured to release a volume of conductive gel from the one or more gel reservoirs to the conductive surface and the skin of the patient in response to a predetermined pressure being applied to the at least one rupturable seal.

4. The device of claim 3, wherein a continuous portion of the at least one rupturable seal, up to and comprising a full perimeter of the at least one rupturable seal, is configured to:
   rupture in response to a force being applied about the perimeter of the at least one rupturable seal; and
   release the volume of conductive gel about a full length of the continuous portion that has ruptured.

5. The device of claim 4, wherein the force being applied to the perimeter of the at least one rupturable seal is between 5.5N/cm$^2$/sec to 15.2N/cm$^2$/sec.

6. The device of claim 3, wherein the predetermined pressure comprises a pressure level in a range of 4-30 psi.

7. The device of claim 1, wherein the one or more ventilation holes of each layer of the multilayer substrate comprises a plurality of ventilation holes of each layer of the multilayer substrate.

8. The device of claim 7, wherein the plurality of ventilation holes are arranged in a pattern within each layer of the multilayer substrate such that at least a portion of each of the plurality of ventilation holes is aligned over a single ventilation hole disposed on the conductive surface to provide air flow to the skin of the patient when the device is worn.

9. The device of claim 1, wherein the multilayer substrate comprises:
an outer layer comprising at least one first substrate ventilation hole;
a diaphragm layer comprising at least one second substrate ventilation hole; and
a lidding layer comprising at least one third substrate ventilation hole,
wherein the at least one first substrate ventilation hole, the at least one second substrate ventilation hole, and the at least one third substrate ventilation hole are aligned over one another.

10. An improved electrotherapy delivery device to promote patient comfort for ambulatory patient use with a wearable defibrillator, the device comprising:
a substrate comprising
an outer layer comprising at least one first substrate ventilation hole,
a diaphragm layer comprising at least one second substrate ventilation hole, and
a lidding layer comprising at least one third substrate ventilation hole,
wherein the at least one first substrate ventilation hole, the at least one second substrate ventilation hole, and the at least one third substrate ventilation hole are aligned to provide air flow to skin of a patient when worn;
one or more gel reservoirs disposed on the substrate and comprising a quantity of gel to be released to the skin of the patient prior to treatment of the patient; and
a conductive surface mechanically coupled to the substrate to impart a therapeutic shock to the skin of a patient, the conductive surface comprising at least one ventilation opening to provide air flow to the skin of the patient, wherein the at least one ventilation opening is larger than any of the at least one first substrate ventilation hole, at least one second substrate ventilation hole, and at least one third substrate ventilation hole.

11. The device of claim 10, wherein the at least one ventilation opening is positioned to at least partially overlap the at least one first substrate ventilation hole, at least one second substrate ventilation hole, and at least one third substrate ventilation hole to provide air flow to the skin of the patient.

12. The device of claim 10, wherein the at least one first substrate ventilation hole comprises a plurality of first substrate ventilation holes, the at least one second substrate ventilation hole comprises a plurality of second substrate ventilation holes, and the at least one third substrate ventilation hole comprises a plurality of third substrate ventilation holes.

13. The device of claim 12, wherein the plurality of first, second, and third substrate ventilation holes are arranged in a pattern such that at least a portion of each of the plurality of first, second, and third substrate ventilation holes are aligned with at least a portion of the at least one ventilation opening when the conductive surface is mechanically coupled to the substrate to provide air flow to the skin of the patient.

14. The device of claim 10, further comprising:
a fluid pressure source in fluid communication with the one or more gel reservoirs; and
at least one rupturable seal in fluid communication with the one or more gel reservoirs, the at least one rupturable seal being configured to release a volume of conductive gel from the one or more gel reservoirs to the conductive surface and the skin of the patient in response to a predetermined pressure being applied to the at least one rupturable seal.

15. The device of claim 14, wherein a continuous portion of the at least one rupturable seal, up to and comprising a full perimeter of the at least one rupturable seal, is configured to:
rupture in response to a force being applied about the perimeter of the at least one rupturable seal; and
release the volume of conductive gel about a full length of the continuous portion that has ruptured.

16. The device of claim 15, wherein the force being applied to the perimeter of the at least one rupturable seal is between 5.5N/cm$^2$/sec to 15.2N/cm$^2$/sec.

17. The device of claim 14, wherein the at least one rupturable seal is configured to distribute the predetermined pressure equally about a perimeter of the at least one rupturable seal.

18. The device of claim 14, wherein the predetermined pressure comprises a pressure level in a range of 4-30 psi.

19. A wearable defibrillator electrotherapy delivery device to promote comfort of an ambulatory patient, the device comprising:
a conductive surface configured to be in electrical contact with skin of the ambulatory patient and provide a therapeutic shock to the patient; and
a substrate including a first plurality of ventilation holes;
wherein the conductive surface includes one or more second ventilation holes, wherein the first plurality of ventilation holes are aligned with the one or more second ventilation holes to provide air flow to the skin of the patient when the device is worn, and wherein the first plurality of ventilation holes includes more ventilation holes compared to the one or more second ventilation holes.

* * * * *